US010520521B2

(12) United States Patent
Johno et al.

(10) Patent No.: US 10,520,521 B2
(45) Date of Patent: Dec. 31, 2019

(54) SUBSTRATE FOR SAMPLE ANALYSIS, SAMPLE ANALYSIS DEVICE, SAMPLE ANALYSIS SYSTEM, AND PROGRAM FOR SAMPLE ANALYSIS SYSTEM

(71) Applicant: PHC HOLDINGS CORPORATION, Tokyo (JP)

(72) Inventors: Masahiro Johno, Ehime (JP); Fusatoshi Okamoto, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 465 days.

(21) Appl. No.: 15/322,977

(22) PCT Filed: Jun. 29, 2015

(86) PCT No.: PCT/JP2015/068724
§ 371 (c)(1),
(2) Date: Dec. 29, 2016

(87) PCT Pub. No.: WO2016/002729
PCT Pub. Date: Jan. 7, 2016

(65) Prior Publication Data
US 2017/0138972 A1     May 18, 2017

(30) Foreign Application Priority Data

Jun. 30, 2014 (JP) ................................. 2014-134779

(51) Int. Cl.
*G01N 35/08* (2006.01)
(52) U.S. Cl.
CPC .................... *G01N 35/08* (2013.01)
(58) Field of Classification Search
CPC ..... B01L 2200/0621; B01L 2200/0668; B01L 2300/0803; B01L 2300/087;
(Continued)

(56) References Cited

U.S. PATENT DOCUMENTS 4,495,295 A    1/1985 Neurath
4,673,653 A    6/1987 Guigan
(Continued)

FOREIGN PATENT DOCUMENTS

EP    0326100 A2    8/1989
EP    0724156 A1    7/1996
(Continued)

OTHER PUBLICATIONS

Extended European Search Report dated Dec. 21, 2017, issued in European Patent Application No. 15814780.1.
(Continued)

*Primary Examiner* — John Fitzgerald
*Assistant Examiner* — Truong D Phan
(74) *Attorney, Agent, or Firm* — McDermott Will & Emery LLP

(57) ABSTRACT

A substrate for sample analysis on which transfer of liquids is to occur with rotational motion, includes a substrate having a rotation axis; a first chamber and a second chamber being located in the substrate and respectively having a first space and a second space for retaining a first liquid and a second liquid; a third chamber being located in the substrate and having a third space for retaining the liquids to be discharged from the first chamber and the second chamber; a first channel having a path connecting the first chamber and the third chamber to transfer the first liquid; and a second channel having a path connecting the second chamber and the third chamber to transfer the second liquid.

24 Claims, 19 Drawing Sheets

(58) Field of Classification Search
CPC ..... B01L 2400/0406; B01L 2400/0409; B01L 2400/0457; B01L 3/50273; B01L 2300/0681; G01N 21/00; G01N 21/07; G01N 33/49; G01N 33/493; G01N 35/00069; G01N 35/08; G01N 21/801; G01N 33/5021; G01N 1/312; F16K 2099/0084; C40B 60/14; B01J 19/0046; B01J 2219/00585
USPC ......... 73/864.81, 863.2, 865.5, 61.42, 61.71, 73/61.72; 422/64, 506, 533, 72; 436/177, 45, 180, 43
See application file for complete search history.

(56) References Cited

U.S. PATENT DOCUMENTS

| | | | |
|---|---|---|---|
| 4,745,077 A | 5/1988 | Holian et al. | |
| 4,916,081 A | 4/1990 | Kamada et al. | |
| 4,918,025 A | 4/1990 | Grenner | |
| 4,990,075 A | 2/1991 | Wogoman | |
| 5,160,702 A | 11/1992 | Kopf-Sill et al. | |
| 5,173,262 A | 12/1992 | Burtis et al. | |
| 5,466,574 A | 11/1995 | Liberti et al. | |
| 5,627,041 A | 5/1997 | Shartle | |
| 5,741,714 A | 4/1998 | Liberti | |
| 5,912,134 A | 6/1999 | Shartle | |
| 6,063,589 A | 5/2000 | Kellogg et al. | |
| 6,103,537 A | 8/2000 | Ullman et al. | |
| 6,238,538 B1 | 5/2001 | Parce et al. | |
| 6,274,384 B1 | 8/2001 | Starzl et al. | |
| 6,458,553 B1 | 10/2002 | Colin et al. | |
| 6,551,841 B1 | 4/2003 | Wilding et al. | |
| 7,476,543 B2 | 1/2009 | Becker et al. | |
| 7,867,753 B2 | 1/2011 | Andersson | |
| 7,897,398 B2* | 3/2011 | Saiki ................. B01L 3/502 422/506 | |
| 8,058,010 B2 | 11/2011 | Erickson et al. | |
| 8,415,140 B2* | 4/2013 | Saiki .................. G01N 33/491 435/286.5 | |
| 8,703,070 B1 | 4/2014 | Parng et al. | |
| 8,956,879 B2* | 2/2015 | Tanaka ................ G01N 33/721 422/73 | |
| 2002/0019059 A1 | 2/2002 | Chow et al. | |
| 2002/0071788 A1 | 6/2002 | Fujii et al. | |
| 2002/0119482 A1 | 8/2002 | Nelson et al. | |
| 2002/0137218 A1 | 9/2002 | Mian et al. | |
| 2002/0151078 A1 | 10/2002 | Kellogg et al. | |
| 2002/0180975 A1 | 12/2002 | Ogura et al. | |
| 2003/0026740 A1 | 2/2003 | Staats | |
| 2003/0077204 A1 | 4/2003 | Seki et al. | |
| 2003/0138819 A1 | 7/2003 | Gong et al. | |
| 2003/0211010 A1 | 11/2003 | Nagaoka et al. | |
| 2004/0089616 A1 | 5/2004 | Kellogg et al. | |
| 2004/0137607 A1 | 7/2004 | Tanaami et al. | |
| 2004/0181343 A1 | 9/2004 | Wigstrom et al. | |
| 2005/0079634 A1 | 4/2005 | Wilding et al. | |
| 2005/0123447 A1 | 6/2005 | Koike et al. | |
| 2005/0178218 A1 | 8/2005 | Montagu | |
| 2005/0221281 A1 | 10/2005 | Ho | |
| 2005/0287577 A1 | 12/2005 | Yamamichi | |
| 2006/0061760 A1 | 3/2006 | Matsumoto et al. | |
| 2006/0263242 A1 | 11/2006 | Yang et al. | |
| 2006/0292641 A1 | 12/2006 | Nakanishi et al. | |
| 2007/0141576 A1 | 6/2007 | Koide | |
| 2007/0160979 A1 | 7/2007 | Andersson | |
| 2007/0166721 A1 | 7/2007 | Phan et al. | |
| 2007/0189927 A1 | 8/2007 | Ballhom et al. | |
| 2007/0218566 A1 | 9/2007 | Barten et al. | |
| 2007/0224304 A1 | 9/2007 | Kunimatsu et al. | |
| 2007/0243111 A1 | 10/2007 | Momose | |
| 2007/0266777 A1 | 11/2007 | Bergman et al. | |
| 2008/0035579 A1 | 2/2008 | Lee et al. | |
| 2008/0073546 A1 | 3/2008 | Andersson et al. | |
| 2008/0102537 A1 | 5/2008 | Harding et al. | |
| 2008/0131978 A1 | 6/2008 | Fujimura et al. | |
| 2008/0138831 A1 | 6/2008 | Hataoka | |
| 2008/0156079 A1 | 7/2008 | Momose | |
| 2008/0171400 A1 | 7/2008 | Cho et al. | |
| 2008/0176272 A1 | 7/2008 | Bergman et al. | |
| 2008/0219891 A1 | 9/2008 | McDevitt et al. | |
| 2008/0240996 A1 | 10/2008 | Harding et al. | |
| 2008/0242556 A1 | 10/2008 | Cao et al. | |
| 2009/0042317 A1 | 2/2009 | Ikeda | |
| 2009/0053108 A1 | 2/2009 | Cho et al. | |
| 2009/0111190 A1 | 4/2009 | Andersson et al. | |
| 2009/0123337 A1 | 5/2009 | Noda et al. | |
| 2009/0126516 A1 | 5/2009 | Yamamoto et al. | |
| 2009/0155125 A1 | 6/2009 | Michiue et al. | |
| 2009/0169430 A1 | 7/2009 | Yamamoto et al. | |
| 2009/0253130 A1 | 10/2009 | Yoo | |
| 2009/0317896 A1 | 12/2009 | Yoo | |
| 2010/0071486 A1 | 3/2010 | Kim et al. | |
| 2010/0074801 A1 | 3/2010 | Saiki | |
| 2010/0078322 A1 | 4/2010 | Yamanishi et al. | |
| 2010/0132820 A1* | 6/2010 | Ozaki ............... G01N 35/00069 137/571 | |
| 2010/0151560 A1 | 6/2010 | Wo et al. | |
| 2010/0159600 A1 | 6/2010 | Shin et al. | |
| 2010/0184228 A1* | 7/2010 | Saiki ....................... B01L 3/502 436/45 | |
| 2010/0221741 A1* | 9/2010 | Saiki .................... G01N 33/491 435/7.1 | |
| 2010/0255589 A1 | 10/2010 | Saiki et al. | |
| 2010/0262389 A1 | 10/2010 | Nakanishi et al. | |
| 2010/0281961 A1 | 11/2010 | Saiki et al. | |
| 2010/0290955 A1 | 11/2010 | Cho et al. | |
| 2011/0045505 A1 | 2/2011 | Warthoe et al. | |
| 2011/0058985 A1* | 3/2011 | Saiki .................... B01L 3/50273 422/69 | |
| 2011/0117665 A1 | 5/2011 | Saiki et al. | |
| 2011/0124128 A1 | 5/2011 | Oosterbroek et al. | |
| 2011/0126646 A1 | 6/2011 | Saiki et al. | |
| 2011/0250695 A1 | 10/2011 | Sarofim et al. | |
| 2012/0024083 A1 | 2/2012 | Wo et al. | |
| 2012/0135533 A1 | 5/2012 | Shikida et al. | |
| 2012/0244607 A1 | 9/2012 | Iwamoto et al. | |
| 2012/0261256 A1 | 10/2012 | Chang et al. | |
| 2012/0269701 A1 | 10/2012 | Linder et al. | |
| 2012/0275971 A1 | 11/2012 | Momose | |
| 2012/0322683 A1 | 12/2012 | Liu et al. | |
| 2013/0029361 A1 | 1/2013 | Hamachi et al. | |
| 2013/0074962 A1 | 3/2013 | Garcia da Fonseca et al. | |
| 2013/0142697 A1 | 6/2013 | Kim et al. | |
| 2013/0164763 A1* | 6/2013 | Saiki .................... G01N 33/491 435/7.25 | |
| 2013/0206701 A1 | 8/2013 | Strohmeier et al. | |
| 2013/0260481 A1 | 10/2013 | Shimizu et al. | |
| 2013/0261010 A1 | 10/2013 | Bailey et al. | |
| 2013/0266956 A1 | 10/2013 | Tia et al. | |
| 2013/0288351 A1 | 10/2013 | Nitta | |
| 2014/0004505 A1 | 1/2014 | Su et al. | |
| 2014/0073041 A1 | 3/2014 | Kijima | |
| 2014/0234184 A1 | 8/2014 | Oshika et al. | |
| 2014/0242721 A1 | 8/2014 | Kellogg et al. | |
| 2014/0270459 A1 | 9/2014 | Moll et al. | |
| 2014/0273192 A1 | 9/2014 | Sharpe et al. | |
| 2015/0087544 A1 | 3/2015 | Putnam et al. | |
| 2015/0093771 A1 | 4/2015 | Griss et al. | |
| 2015/0098864 A1 | 4/2015 | Yang | |
| 2015/0111778 A1 | 4/2015 | McDevitt et al. | |
| 2015/0251183 A1 | 9/2015 | Saiki | |
| 2015/0355132 A1 | 12/2015 | Crooks et al. | |
| 2017/0131304 A1 | 5/2017 | Johno et al. | |
| 2017/0131305 A1 | 5/2017 | Okamoto et al. | |
| 2017/0350910 A1* | 12/2017 | Okamoto ............... G01N 35/08 | |

FOREIGN PATENT DOCUMENTS

| | | |
|---|---|---|
| EP | 0871539 A1 | 10/1998 |
| EP | 1105457 A1 | 6/2001 |
| EP | 2072134 A2 | 6/2009 |
| EP | 2133150 A1 | 12/2009 |

(56) References Cited

FOREIGN PATENT DOCUMENTS

| | | |
|---|---|---|
| EP | 2 175 278 A1 | 4/2010 |
| EP | 2253958 A1 | 11/2010 |
| EP | 2311565 A1 | 4/2011 |
| EP | 2402460 A1 | 1/2012 |
| EP | 2602025 A1 | 6/2013 |
| JP | S60-159651 A | 8/1985 |
| JP | 361-264263 A | 11/1986 |
| JP | H01-227061 A | 9/1989 |
| JP | H05-297001 A | 11/1993 |
| JP | H05-322894 A | 12/1993 |
| JP | H07-500910 A | 1/1995 |
| JP | H08-262024 A | 10/1996 |
| JP | H09-218201 A | 8/1997 |
| JP | H09-257796 A | 10/1997 |
| JP | H09-325148 A | 12/1997 |
| JP | H10-300752 A | 11/1998 |
| JP | 2001-502793 A | 2/2001 |
| JP | 2002-236131 A | 8/2002 |
| JP | 2003-043052 A | 2/2003 |
| JP | 2004-163104 A | 6/2004 |
| JP | 2005-010031 A | 1/2005 |
| JP | 2005-345160 A | 12/2005 |
| JP | 2006-010535 A | 1/2006 |
| JP | 2006-068384 A | 3/2006 |
| JP | 2006-112824 A | 4/2006 |
| JP | 2006-177850 A | 7/2006 |
| JP | 2006-258696 A | 9/2006 |
| JP | 2007-003361 A | 1/2007 |
| JP | 2007-003414 A | 1/2007 |
| JP | 2007-010341 A | 1/2007 |
| JP | 2007-024851 A | 2/2007 |
| JP | 2007-047031 A | 2/2007 |
| JP | 2007-064742 A | 3/2007 |
| JP | 2007-071557 A | 3/2007 |
| JP | 2007-071655 A | 3/2007 |
| JP | 2007-078676 A | 3/2007 |
| JP | 2007-101240 A | 4/2007 |
| JP | 2007-279069 A | 10/2007 |
| JP | 2007-285792 A | 11/2007 |
| JP | 2007-530938 A | 11/2007 |
| JP | 2007-315879 A | 12/2007 |
| JP | 2008-064701 A | 3/2008 |
| JP | 2008-064748 A | 3/2008 |
| JP | 2008-128906 A | 6/2008 |
| JP | 2008-134126 A | 6/2008 |
| JP | 2008-157708 A | 7/2008 |
| JP | 2008-164360 A | 7/2008 |
| JP | 2008-164434 A | 7/2008 |
| JP | 2008-216237 A | 9/2008 |
| JP | 2009-014529 A | 1/2009 |
| JP | 2009-031116 A | 2/2009 |
| JP | 2009-042104 A | 2/2009 |
| JP | 2009-109251 A | 5/2009 |
| JP | 2009-121860 A | 6/2009 |
| JP | 2009-128342 A | 6/2009 |
| JP | 2009-133831 A | 6/2009 |
| JP | 2009-139289 A | 6/2009 |
| JP | 2009-156717 A | 7/2009 |
| JP | 2009-156778 A | 7/2009 |
| JP | 2009-162701 A | 7/2009 |
| JP | 2009-180688 A | 8/2009 |
| JP | 2009-180697 A | 8/2009 |
| JP | 2009-186296 A | 8/2009 |
| JP | 2009-210564 A | 9/2009 |
| JP | 2009-287971 A | 12/2009 |
| JP | 2010-071644 A | 4/2010 |
| JP | 2010-122022 A | 6/2010 |
| JP | 2010-151447 A | 7/2010 |
| JP | 2010-210531 A | 9/2010 |
| JP | 2010-243373 A | 10/2010 |
| JP | 2010-286297 A | 12/2010 |
| JP | 2011-007778 A | 1/2011 |
| JP | 2011-069618 A | 4/2011 |
| JP | 2011-183589 A | 9/2011 |
| JP | 2011-196849 A | 10/2011 |
| JP | 2012-143204 A | 8/2012 |
| JP | 2012-159325 A | 8/2012 |
| JP | 2012-215515 A | 11/2012 |
| JP | 2012-229985 A | 11/2012 |
| JP | 2013-050435 A | 3/2013 |
| JP | 2013-079812 A | 5/2013 |
| JP | 2013-205305 A | 10/2013 |
| JP | 2014-032018 A | 2/2014 |
| JP | 2014-044077 A | 3/2014 |
| JP | 2014-048209 A | 3/2014 |
| JP | 2014-106207 A | 6/2014 |
| JP | 2014-190906 A | 10/2014 |
| JP | 2014-232023 A | 12/2014 |
| JP | 2015-121493 A | 7/2015 |
| JP | 2015-197338 A | 11/2015 |
| JP | 2015-223562 A | 12/2015 |
| WO | 90/013016 A1 | 11/1990 |
| WO | 90/015321 A2 | 12/1990 |
| WO | 92/016844 A1 | 10/1992 |
| WO | 93/08893 A1 | 5/1993 |
| WO | 96/026011 A1 | 8/1996 |
| WO | 98/13684 A1 | 4/1998 |
| WO | 1999/064836 A1 | 12/1999 |
| WO | 01/087485 A2 | 11/2001 |
| WO | 02/23163 A1 | 3/2002 |
| WO | 05/075997 A1 | 8/2005 |
| WO | 2007/005077 A1 | 1/2007 |
| WO | 2007/105584 A1 | 9/2007 |
| WO | 2007/116909 A1 | 10/2007 |
| WO | 07/122943 A1 | 11/2007 |
| WO | 2008/053743 A1 | 5/2008 |
| WO | 2008/139697 A1 | 11/2008 |
| WO | 2010/044598 A2 | 4/2010 |
| WO | 10/058303 A1 | 5/2010 |
| WO | 2010/077159 A1 | 7/2010 |
| WO | 2012/164552 A1 | 12/2012 |
| WO | 2014/017018 A1 | 1/2014 |

OTHER PUBLICATIONS

Chinese Search Report issued in Chinese Patent Application No. 201580035558.6, dated Dec. 15, 2017; with partial English translation.
Non-Final Office Action issued in related U.S. Appl. No. 15/323,001, dated Jun. 3, 2019.
Final Office Action issued in related U.S. Appl. No. 15/323,007, dated May 16, 2019.
International Search Report issued in corresponding International Patent Application No. PCT/JP2015/068729, dated Sep. 1, 2015; with English translation.
International Search Report issued in corresponding International Patent Application No. PCT/JP2015/068724, dated Sep. 1, 2015; with English translation.
International Search Report issued in corresponding International Patent Application No. PCT/JP2015/068723, dated Sep. 29, 2015; with English translation.
International Search Report issued in corresponding International Patent Application No. PCT/JP2015/068722, dated Sep. 29, 2015; with English translation.
Non-Final Office Action issued in related U.S. Appl. No. 15/323,007, dated Jan. 4, 2019.
International Search Report issued in International Patent Application No. PCT/JP2015/084738, dated Mar. 15, 2016; with English translation.
Extended European Search Report issued in European Patent Application No. 15866519.0, dated Jun. 19, 2018.
Notice of Allowance issued in related U.S. Appl. No. 15/322,910, dated Feb. 25, 2019.

* cited by examiner

SUBSTRATE FOR SAMPLE ANALYSIS, SAMPLE ANALYSIS DEVICE, SAMPLE ANALYSIS SYSTEM, AND PROGRAM FOR SAMPLE ANALYSIS SYSTEM

RELATED APPLICATIONS

This application is the U.S. National Phase under 35 U.S.C. § 371 of International Patent Application No. PCT/JP2015/068724, filed on Jun. 29, 2015, which in turn claims the benefit of Japanese Application No. 2014-134779, filed on Jun. 30, 2014, the disclosures of which Applications are incorporated by reference herein.

TECHNICAL FIELD

The present application relates to a substrate for sample analysis, a sample analysis device, a sample analysis system, and a program for a sample analysis system.

BACKGROUND ART

Techniques have been known which utilize a substrate for sample analysis in order to analyze a specific component within an analyte, such as urine or blood. For example, Patent Document 1 discloses a technique that utilizes a disk-shaped substrate for sample analysis, on which channels, chambers, and the like are formed. In this technique, the substrate for sample analysis is allowed to rotate, etc., thereby effecting transfer, distribution, mixing of solutions, analysis of components within an analyte solution, and so on.

CITATION LIST

Patent Literature

[Patent Document 1] Japanese National Phase PCT Laid-Open Publication No. 7-500910

SUMMARY OF INVENTION

Technical Problem

Analysis of specific components within an analyte includes assay techniques which utilize enzymatic reaction, immunoreaction, and the like, and involve complicated reaction steps. There has been a desire for a technique which allows assay techniques that involve such complicated reaction steps to be performed in a substrate for sample analysis.

A non-limiting, illustrative embodiment of the present application provides a substrate for sample analysis, a sample analysis device, a sample analysis system, and a program for a sample analysis system which support assay techniques that carry out analysis of components within an analyte through more complicated reaction steps.

Solution to Problem

A substrate for sample analysis according to one aspect of the present application is a substrate for sample analysis on which transfer of liquids is to occur with rotational motion, the substrate for sample analysis comprising: a substrate having a rotation axis; a first chamber and a second chamber being located in the substrate and respectively having a first space and a second space for retaining a first liquid and a second liquid; a third chamber being located in the substrate and having a third space for retaining the liquids to be discharged from the first chamber and the second chamber; a first channel having a path connecting the first chamber and the third chamber to transfer the first liquid; and a second channel having a path connecting the second chamber and the third chamber to transfer the second liquid, wherein, in rotating the substrate either clockwise or counterclockwise around the rotation axis while supporting the substrate so that the rotation axis of the substrate is inclined at an angle which is greater than 0° but not more than 90° with respect to the direction of gravity, when the substrate is rotated by an angle A1 from an arbitrary predetermined reference angle at which the first liquid and the second liquid retained in the first chamber and the second chamber are not transferred to the third chamber via the first channel and the second channel, respectively, a first predetermined amount of first liquid moves from the first chamber to the third chamber, and a second predetermined amount of second liquid moves from the second chamber to the third chamber; and when the substrate is further rotated by an angle A2 from the angle A1, a third predetermined amount of first liquid moves from the first chamber to the third chamber, and a fourth predetermined amount of second liquid moves from the second chamber to the third chamber.

Advantageous Effects of Invention

A substrate for sample analysis, a sample analysis device, a sample analysis system, and a program for a sample analysis system according to one aspect of the present application support assay techniques that carry out analysis of components within an analyte through assay techniques that carry out analysis of components within an analyte through complicated reaction steps.

DESCRIPTION OF EMBODIMENTS

Assay techniques for components within an analyte such as urine or blood may utilize a combination reaction between the analyte being the subject for analysis and a ligand which specifically binds to the analyte. Examples of such assay techniques include immunoassay techniques and genetic diagnosis techniques.

Examples of immunoassay techniques are competitive assays and non-competitive assays (sandwich immunoassay). Examples of genetic diagnosis techniques are genetic detection techniques based on hybridization. In these immunoassay techniques and genetic detection techniques, magnetic particles (which may also be referred to as "magnetic beads", "magnetism particles", "magnetism beads", etc.) are used, for example. As an example of such assay techniques, a sandwich immunoassay utilizing magnetic particles will be specifically described.

Figure 1:
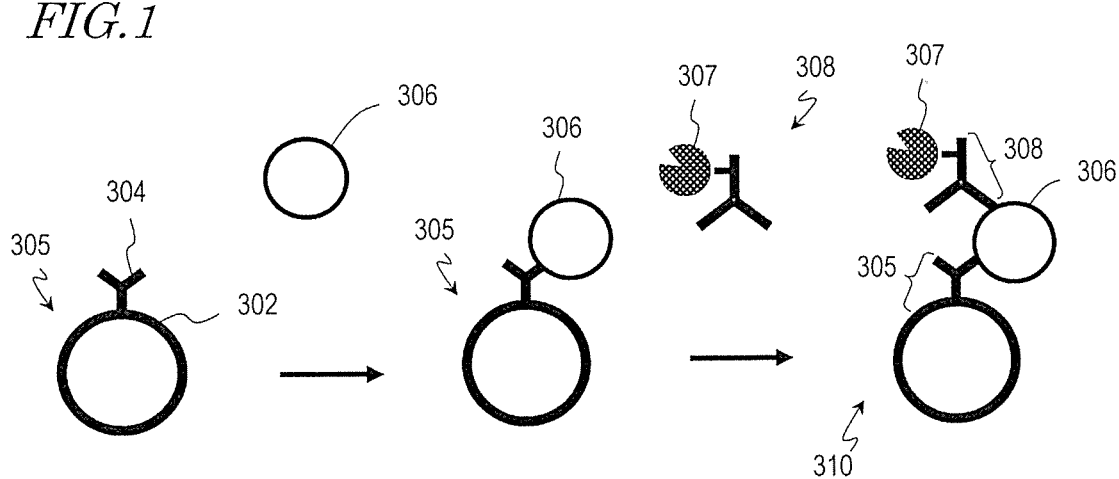
FIG. 1 An exemplary schematic diagram describing a sandwich immunoassay utilizing magnetic particles.

As shown in FIG. 1, first, a primary antibody 304 having a magnetic particle 302 immobilized to whose surface (hereinafter referred to as the "magnetic-particle-immobilized antibody 305") and an antigen 306, for which measurements are to be taken, are allowed to bind through an antigen-antibody reaction. Next, a secondary antibody to which a label substance 307 has bound (hereinafter referred to as a "labeled antibody 308") and the antigen 306 are allowed to bind through an antigen-antibody reaction. As a result, a composite 310 is obtained in which the magnetic-particle-immobilized antibody 305 and the labeled antibody 308 have bound to the antigen 306.

A signal which is based on the label substance 307 of the labeled antibody 308 that has bound to the composite 310 is detected, and an antigen concentration is measured in accordance with the amount of detected signal. Examples of the label substance 307 include enzymes (e.g., peroxidase, alkaline phosphatase, and luciferase), chemiluminescent substances, electrochemiluminescent substances, and fluorescent substances. In accordance with each such label substance 307, dye, luminescence, fluorescence, or other signals are detected.

In this series of reactions, in order to obtain the composite 310 as the reaction product, separation needs to be effected between unreacted substance in the analyte, substance that has non-specifically adsorbed to the magnetic particles or the like, and unreacted substance which was not involved in the formation of the composite 310 (e.g., the labeled antibody 308). This separation is called B/F separation (Bound/Free Separation). A B/F separation process is similarly required also in immunoassay techniques based on competitive assays and in genetic detection techniques based on hybridization. Examples of not using magnetic particles may include the use of: a ligand which is immobilized through physisorption to a solid phase composed of polystyrene, polycarbonate, or other materials, a ligand which is immobilized to a solid phase through physisorption via a chemical bond, a ligand which is immobilized to a solid phase via a chemical bond, a ligand which is immobilized to the surface of a metal substrate composed of gold or the like (e.g., being immobilized by using a self-assembled monolayer (SAM)), and so on.

In order to perform adequate B/F separation, it is preferable to wash magnetic particles including the composite 310 multiple times with a wash solution. Specifically, first, from the reaction solution that contains the composite 310, the unreacted antigen 306, the labeled antibody 308, and the like, only the reaction solution is removed while keeping the composite 310 containing the magnetic particles captured with a magnet. Thereafter, a wash solution is added and the composite 310 is washed, and the wash solution is removed. By repeating such washing multiple times, a B/F separation can be attained such that the unreacted substance and the non-specifically adsorbed substance are sufficiently removed.

Conventionally, a maneuver involving such multiple washes may be manually performed by an operator using analysis equipment, or achieved by a large-sized analysis apparatus with a complicated mechanism. Therefore, there has been a desire for a technique that achieves multiple washes in an easier manner.

By using a substrate for sample analysis as disclosed in Patent Document 1, the inventors have investigated into a technique that enables multiple wash processes, thus arriving at a novel substrate for sample analysis, sample analysis device, sample analysis system, and program for a sample analysis system. A substrate for sample analysis, a sample analysis device, a sample analysis system, and a program for a sample analysis system according to one aspect of the present application are as follows.

[Item 1] A substrate for sample analysis on which transfer of liquids is to occur with rotational motion, the substrate for sample analysis comprising:
a substrate having a rotation axis;
a first chamber and a second chamber being located in the substrate and respectively having a first space and a second space for retaining a first liquid and a second liquid;
a third chamber being located in the substrate and having a third space for retaining the liquids to be discharged from the first chamber and the second chamber;
a first channel having a path connecting the first chamber and the third chamber in the substrate to transfer the first liquid; and
a second channel having a path connecting the second chamber and the third chamber in the substrate to transfer the second liquid, wherein,
in rotating the substrate clockwise or counterclockwise around the rotation axis while supporting the substrate so that the rotation axis of the substrate is inclined at an angle which is greater than 0° but not more than 90° with respect to the direction of gravity,
when the substrate is rotated by an angle A1 from an arbitrary predetermined reference angle at which the first liquid and the second liquid retained in the first chamber and the second chamber are not transferred to the third chamber via the first channel and the second channel, respectively,
a first predetermined amount of first liquid moves from the first chamber to the third chamber, and
a second predetermined amount of second liquid moves from the second chamber to the third chamber; and
when the substrate is further rotated by an angle A2 from the angle A1,
a third predetermined amount of first liquid moves from the first chamber to the third chamber, and
a fourth predetermined amount of second liquid moves from the second chamber to the third chamber.

[Item 2] The substrate for sample analysis of item 1, wherein,
the substrate includes
a first side face defining a portion of the first space in the substrate and adjoining the first channel, and a third side face adjoining the first side face, and
a second side face defining a portion of the second space in the substrate and adjoining the second channel, and a fourth side face adjoining the second side face; and
when the substrate is retained at the arbitrary predetermined reference angle while supporting the substrate so that the rotation axis of the substrate is inclined at an angle which is greater than 0° but not more than 90° with respect to the direction of gravity,
the first chamber retains the first liquid at least with the first side face and the third side face, and
the second chamber retains the second liquid at least with the second side face and the fourth side face.

[Item 3] The substrate for sample analysis of item 2, wherein a first boundary position between the first side face and the first channel is defined by a boundary between a liquid surface of the first wash solution and the first channel or the first side face that exists when, in rotating the substrate from the arbitrary predetermined reference angle to the angle A1, the first liquid first begins to move toward the third chamber at a position along a predetermined thickness direction.

[Item 4] The substrate for sample analysis of item 3, wherein a second boundary position between the second side face and the second channel is defined by a boundary between a liquid surface of the second wash solution and the second channel or the second side face that exists when, in rotating the substrate from the arbitrary predetermined reference angle to the angle A2, the second liquid first begins to move toward the third chamber at a position along the predetermined thickness direction.

[Item 5] The substrate for sample analysis of item 4, wherein,
in a case where the first boundary position is closer to the rotation axis than is the first side face and the second boundary position is closer to the rotation axis than is the second side face, or
in a case where the first boundary position is more distant from the rotation axis than is the first side face and the second boundary position is more distant from the rotation axis than is the second side face,
when the substrate is viewed from a direction which is parallel to the rotation axis in a state where the substrate is retained at the arbitrary predetermined reference angle while supporting the substrate so that the rotation axis of the substrate is inclined at an angle which is greater than 0° but not more than 90° with respect to the direction of gravity, the first boundary position and second boundary position are on either a right or left side on the substrate; and
a direction of rotation in which the substrate is rotated by the angle A1 from the arbitrary predetermined reference angle and a direction of rotation in which the substrate is rotated by the angle A2 from the angle A1 are an identical direction.

[Item 6] The substrate for sample analysis of item 4, wherein, in a case where the first boundary position is closer to the rotation axis than is the first side face and the second boundary position is closer to the rotation axis than is the second side face, or in a case where the first boundary position is more distant from the rotation axis than is the first side face and the second boundary position is more distant from the rotation axis than is the second side face, when the substrate is viewed from a direction which is parallel to the rotation axis in a state where the substrate is retained at the arbitrary predetermined reference angle while supporting the substrate so that the rotation axis of the substrate is inclined at an angle which is greater than 0° but not more than 90° with respect to the direction of gravity, the first boundary position and second boundary position are respectively on different right or left sides on the substrate, a direction of rotation in which the substrate is rotated by the angle A1 from the arbitrary predetermined reference angle and a direction of rotation in which the substrate is rotated by the angle A2 from the angle A1 are opposite directions.

[Item 7] The substrate for sample analysis of item 4, wherein, in a case where the first boundary position is closer to the rotation axis than is the first side face and the second boundary position is more distant from the rotation axis than is the second side face, or in a case where the first boundary position is more distant from the rotation axis than is the first side face and the second boundary position is closer to the rotation axis than is the second side face, when the substrate is viewed from a direction which is parallel to the rotation axis in a state where the substrate is retained at the arbitrary predetermined reference angle while supporting the substrate so that the rotation axis of the substrate is inclined at an angle which is greater than 0° but not more than 90° with respect to the direction of gravity, the first boundary position and second boundary position respectively on different right or left sides on the substrate; and a direction of rotation in which the substrate is rotated by the angle A1 from the arbitrary predetermined reference angle and a direction of rotation in which the substrate is rotated by the angle A2 from the angle A1 are an identical direction.

[Item 8] The substrate for sample analysis of item 4, wherein, in a case where the first boundary position is closer to the rotation axis than is the first side face and the second boundary position is more distant from the rotation axis than is the second side face, or in a case where the first boundary position is more distant from the rotation axis than is the first side face and the second boundary position is closer to the rotation axis than is the second side face, when the substrate is viewed from a direction which is parallel to the rotation axis in a state where the substrate is retained at the arbitrary predetermined reference angle while supporting the substrate so that the rotation axis of the substrate is inclined at an angle which is greater than 0° but not more than 90° with respect to the direction of gravity, the first boundary position and second boundary position are on either a right or left side on the substrate, a direction of rotation in which the substrate is rotated by the angle A1 from the arbitrary predetermined reference angle and a direction of rotation in which the substrate is rotated by the angle A2 from the angle A1 are opposite directions.

[Item 9] The substrate for sample analysis of item 1, wherein the first channel and the second channel respectively transfer the first liquid and the second liquid based on gravity.

[Item 10] The substrate for sample analysis of item 9, wherein, when the substrate is retained at the arbitrary predetermined reference angle while supporting the substrate so that the rotation axis of the substrate is inclined at an angle which is greater than 0° but not more than 90° with respect to the direction of gravity, the third chamber is situated below the first chamber and the second chamber along the direction of gravity.

[Item 11] The substrate for sample analysis of item 1, wherein the second predetermined amount is zero.

[Item 12] The substrate for sample analysis of item 11, wherein the fourth predetermined amount is the entire amount of second liquid that is retained in the second chamber.

[Item 13] The substrate for sample analysis of item 1, wherein the first predetermined amount is the entire amount of first liquid that is retained in the first chamber, and the third predetermined amount is zero.

[Item 14] The substrate for sample analysis of item 1, wherein, the first predetermined amount is the entire amount of first liquid that is retained in the first chamber;

the second predetermined amount is zero;

the third predetermined amount is zero; and the fourth predetermined amount is the entire amount of second liquid that is retained in the second chamber.

[Item 15] A substrate for sample analysis on which transfer of liquids is to occur with rotational motion, the substrate for sample analysis comprising:

a substrate having a rotation axis;

a first chamber and a second chamber being located in the substrate and respectively having a first space and a second space for retaining a first liquid and a second liquid;

a third chamber being located in the substrate and having a third space for retaining the liquids to be discharged from the first chamber and the second chamber;

a first channel having a path connecting the first chamber and the third chamber to transfer the first liquid; and a second channel having a path connecting the second chamber and the third chamber to transfer the second liquid, wherein, the substrate includes, in the substrate, a first side face and a second side face adjoining the first channel and the second channel respectively defining a portion of the first space and a portion of the second space, and a third side face and a fourth side face respectively adjoining the first side face and the second side face;

the first chamber forms a recess with the first side face and the third side face;

the second chamber forms a recess with the second side face and the fourth side face;

the recess of the first chamber and the recess of the second chamber constitute dented shapes which are oriented in a same direction as each other; and when viewed from a direction which is parallel to the rotation axis, the first side face and the second side face are not parallel.

[Item 16] The substrate for sample analysis of item 15, wherein, when viewed from a direction which is parallel to the rotation axis, the first side face and the second side face are not parallel.

[Item 17] The substrate for sample analysis of item 15 or 16, wherein the first channel and the second channel respectively transfer the first liquid and the second liquid based on gravity.

[Item 18] The substrate for sample analysis of item 17, wherein,
when the substrate is retained at the arbitrary predetermined reference angle while supporting the substrate so that the rotation axis of the substrate is inclined at an angle which is greater than 0° but not more than 90° with respect to the direction of gravity,
the third chamber is situated below the first chamber and the second chamber along the direction of gravity.

[Item 19] The substrate for sample analysis of item 17, wherein the first channel and the second channel respectively transfer the first liquid and the second liquid via capillary action.

[Item 20] The substrate for sample analysis of any of items 15 to 19, wherein, in rotating the substrate clockwise or counterclockwise around the rotation axis while supporting the substrate so that the rotation axis of the substrate is inclined at an angle which is greater than 0° but not more than 90° with respect to the direction of gravity, at a predetermined reference rotation angle, the substrate is able to retain all of the first liquid with the first side face and the third side face and retain all of the second liquid with the second side face and the fourth side face.

[Item 21] The substrate for sample analysis of item 20, further comprising:
a fourth chamber being in the substrate located more distant from the rotation axis than is the third chamber and having a fourth space for retaining at least one of the first liquid or the second liquid to be discharged from the third chamber; and
a third channel being located in the substrate and having a path connecting the third chamber and the fourth chamber, the third channel capable of being filled via capillary action with the liquid that is retained in the third space.

[Item 22] The substrate for sample analysis of item 21, wherein,
the third channel includes a first bent portion which is convex toward an opposite side from the rotation axis and a second bent portion which is convex toward the rotation axis, the first bent portion being located between the second bent portion and the third chamber;
a distance from the rotation axis to the fourth chamber is longer than a distance from the rotation axis to an apex of the first bent portion; and
a distance from the rotation axis to a liquid surface of the liquid that is retained in the third chamber as created by a centrifugal force due to rotation of the substrate is longer than a distance from the rotation axis to an apex of the second bent portion.

[Item 23] The substrate for sample analysis of any of items 1 to 22, further comprising a magnet located near the third chamber.

[Item 24] A sample analysis system comprising:
the substrate for sample analysis of any of items 1 to 20; and
a sample analysis device, including a motor to rotate the substrate for sample analysis around the rotation axis in a state where the rotation axis is inclined at an angle which is greater than 0° but not more than 90° with respect to the direction of gravity,
an angle detection circuit to detect an angle of a shaft of the motor,
a drive circuit to control rotation and a stopping angle of the motor based on a result of detection by the angle detection circuit, and
a control circuit including an arithmetic unit, a memory, and a program which is stored in the memory and executable by the arithmetic unit, to control based on the program an operation of the motor, the angle detection circuit, the origin detector, and the drive circuit,
wherein,
when the substrate for sample analysis with the first chamber and the second chamber being filled respectively with the first liquid and the second liquid is placed on a turntable of the sample analysis device,
the program
(a) stops the substrate for sample analysis at a predetermined first angle to transfer the first liquid in the first chamber through the first channel to the third chamber, and
(b) stops the substrate for sample analysis at a predetermined second angle to transfer the second liquid in the second chamber through the second channel to the third chamber.

[Item 25] The sample analysis system of item 24, wherein, the substrate for sample analysis further includes
a fourth chamber being in the substrate located more distant from the rotation axis than is the third chamber and having a fourth space for retaining at least one of the first liquid or the second liquid to be discharged from the third chamber, and
a third channel being located in the substrate and having a path connecting the third chamber and the fourth chamber, the third channel capable of being filled via capillary action with the liquid that is retained in the third space; and
between the processes (a) and (b), the program,
(c) with a centrifugal force due to rotation of the substrate, rotates the substrate for sample analysis at a rate causing a centrifugal force which is stronger than a capillary force to act on the liquid filling the third channel, to move the first liquid in the third chamber through the third channel to the fourth chamber.

[Item 26] The sample analysis system of item 24 or 25, wherein, after the process (b), the program,
(d) with a centrifugal force due to rotation of the substrate, rotates the substrate for sample analysis at a rate causing a centrifugal force which is stronger than a capillary force to act on the liquid filling the third channel, to move the second liquid in the third chamber through the third channel to the fourth chamber.

[Item 27] A sample analysis device comprising:
a motor to rotate the substrate for sample analysis of items 1 to 19 around the rotation axis in a state where the rotation axis is inclined at an angle which is greater than 0° but not more than 90° with respect to the direction of gravity;
an angle detection circuit to detect an angle of a shaft of the motor;
a drive circuit to control rotation and a stopping angle of the motor based on a result of detection by the angle detection circuit; and
a control circuit including an arithmetic unit, a memory, and a program which is stored in the memory and executable by the arithmetic unit, to control based on the program an operation of the motor, the angle detection circuit, and the drive circuit, wherein,
when the substrate for sample analysis with the first chamber and the second chamber being filled respectively with the first liquid and the second liquid is placed on a turntable of the sample analysis device,
the program
(a) stops the substrate for sample analysis at a predetermined first angle to transfer the first liquid in the first chamber through the first channel to the third chamber, and
(b) stops the substrate for sample analysis at a predetermined second angle to transfer the second liquid in the second chamber through the second channel to the third chamber.

[Item 28] The sample analysis device of item 27, wherein, the substrate for sample analysis further includes
a fourth chamber being in the substrate located more distant from the rotation axis than is the third chamber and having a fourth space for retaining at least one of the first liquid or the second liquid to be discharged from the third chamber, and
a third channel being located in the substrate and having a path connecting the third chamber and the fourth chamber, the third channel capable of being filled via capillary action with the liquid that is retained in the third space; and
between the processes (a) and (b), the program,
(c) with a centrifugal force due to rotation of the substrate, rotates the substrate for sample analysis at a rate causing a centrifugal force which is stronger than a capillary force to act on the liquid filling the third channel, to move the first liquid in the third chamber through the third channel to the fourth chamber.

[Item 29] The sample analysis device of item 27 or 28, wherein, after the process (b), the program,
(d) with a centrifugal force due to rotation of the substrate, rotates the substrate for sample analysis at a rate causing a centrifugal force which is stronger than a capillary force to act on the liquid filling the third channel, to move the second liquid in the third chamber through the third channel to the fourth chamber.

[Item 30] A program for a sample analysis system comprising:
the substrate for sample analysis of any of items 1 to 19; and
a sample analysis device, including
a motor to rotate the substrate for sample analysis around the rotation axis in a state where the rotation axis is inclined at an angle which is greater than 0° but not more than 90° with respect to the direction of gravity,
an angle detection circuit to detect an angle of a shaft of the motor,
a drive circuit to control rotation and a stopping angle of the motor based on a result of detection by the angle detection circuit, and
a control circuit including an arithmetic unit, a memory, and a program which is stored in the memory and executable by the arithmetic unit, to control based on the program an operation of the motor, the angle detection circuit, the origin detector, and the drive circuit,
wherein,
when the substrate for sample analysis with the first chamber and the second chamber being filled respectively with the first liquid and the second liquid is placed on a turntable of the sample analysis device,
the program
(a) stops the substrate for sample analysis at a predetermined first angle to transfer the first liquid in the first chamber through the first channel to the third chamber, and
(b) stops the substrate for sample analysis at a predetermined second angle to transfer the second liquid in the second chamber through the second channel to the third chamber.

[Item 31] The program for a sample analysis system of item 30, wherein,
the substrate for sample analysis further includes
a fourth chamber being in the substrate located more distant from the rotation axis than is the third chamber and having a fourth space for retaining at least one of the first liquid or the second liquid to be discharged from the third chamber, and
a third channel being located in the substrate and having a path connecting the third chamber and the fourth chamber, the third channel capable of being filled via capillary action with the liquid that is retained in the third space; and
between the processes (a) and (b), the program,
(c) with a centrifugal force due to rotation of the substrate, rotates the substrate for sample analysis at a rate causing a centrifugal force which is stronger than a capillary force to act on the liquid filling the third channel, to move the first liquid in the third chamber through the third channel to the fourth chamber.

[Item 32] The program for a sample analysis system of item 30 or 31, wherein, after the process (b), the program,
(d) with a centrifugal force due to rotation of the substrate, rotates the substrate for sample analysis at a rate causing a centrifugal force which is stronger than a capillary force to act on the liquid filling the third channel, to move the second liquid in the third chamber through the third channel to the fourth chamber.

Hereinafter, with reference to the drawings, the substrate for sample analysis, sample analysis device, sample analysis system, and program for a sample analysis system according to the present embodiment will be described in detail. The substrate for sample analysis, sample analysis device, sample analysis system, and program for a sample analysis system according to the present embodiment are able to transfer a liquid which is retained in each of two or more chambers to the same chamber at different points in time. Although the embodiment will illustrate the liquid(s) to be a wash solution(s), the liquid(s) may be any of various liquids for use in sample analysis, without being limited to a wash solution(s).

Figure 2A:
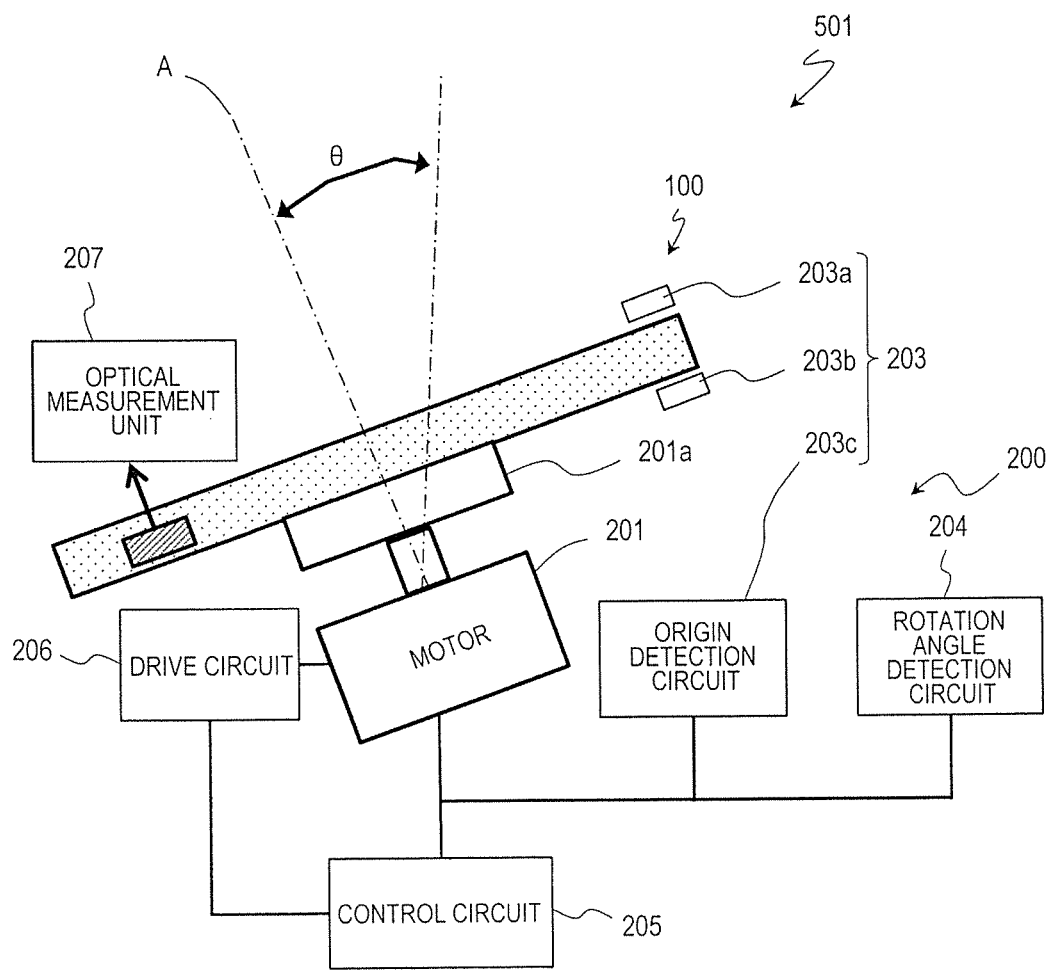
FIG. 2A An exemplary schematic diagram showing the construction of a sample analysis system according to an embodiment.
Figure 2B:
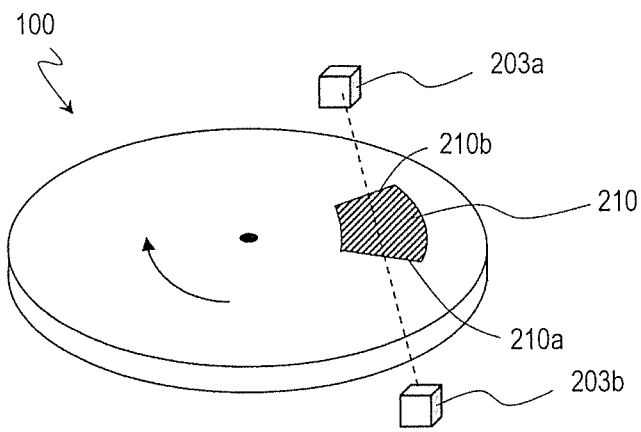
FIG. 2B An exemplary schematic diagram showing a construction for detecting an origin of a substrate for sample analysis in a sample analysis system.

FIG. 2 is a schematic diagram showing an overall construction of the sample analysis system 501. The sample analysis system 501 includes a substrate 100 for sample analysis and a sample analysis device 200.

(Construction of the Sample Analysis Device 200)

The sample analysis device 200 includes a motor 201, an origin detector 203, a rotation angle detection circuit 204, a control circuit 205, a drive circuit 206, and an optical measurement unit 207.

The motor 201 includes a turntable 201*a* and a shaft A which is tilted from the direction of gravity at an angle θ which is greater than 0° but not more than 90° with respect to the direction of gravity, and rotates the substrate 100 for sample analysis placed on the turntable 201*a* around the shaft A. Since the shaft A is tilted, not only a centrifugal force due to rotation but a gravity-based transfer can also be utilized for causing a transfer of any liquid in the substrate 100 for sample analysis. The angle of tilt of the shaft A with respect to the direction of gravity is preferably 5° or more, more preferably not less than 10° and not more than 45°, and still more preferably not less than 20° and not more than 30°. The motor 201 may be a DC motor, a brushless motor, an ultrasonic motor, or the like, for example.

The origin detector 203 detects an origin of the substrate 100 for sample analysis which is attached to the motor 201. For example, the origin detector 203 includes a light source 203a, a photodetector 203b, and an origin detection circuit 203c, and is disposed so that the substrate 100 for sample analysis comes between the light source 203a and the photodetector 203b. For example, the light source 203a may be a light-emitting diode, and the photodetector 203b may be a photodiode. The substrate 100 for sample analysis has a marker 210 at a specific position. The marker 210 has a light shielding ability to shade at least part of the light which exits the light source 203a, for example. The substrate 100 for sample analysis has a small transmittance (e.g. 10% or less) in the region of the marker 210, and a large transmittance (e.g. 60% or more) in the region other than the marker 210.

As the substrate 100 for sample analysis is rotated by the motor 201, the photodetector 203b outputs a detection signal which is in accordance with the amount of incident light on the origin detection circuit 203c. Depending on the direction of rotation, the detection signal may increase or decrease at an edge 210a and at an edge 210b of the marker 210. The origin detection circuit 203c detects a decrease in the amount of detected light and outputs it as an origin signal, for example, while the substrate 100 for sample analysis is rotating clockwise as indicated by the arrow. In the present specification, the position of the edge 210a of the marker 210 will be regarded as the origin position of the substrate 100 for sample analysis (i.e., a reference angular position of the substrate 100 for sample analysis). However, a position at any specific angle, as arbitrarily determined from the position of the edge 210a of the marker 210, might be defined as an origin. In the case where the marker 210 has a sector shape, with a central angle being smaller than the precision of angle detection that is required for sample analysis, the marker 210 itself may be regarded as the origin position.

The origin position is utilized by the sample analysis device 200 in acquiring information on the rotation angle of the substrate 100 for sample analysis.

The origin detector 203 may have any other construction. For example, a magnet for use in origin detection may be provided on the substrate 100 for sample analysis, and, instead of the photodetector 203b, the origin detector 203 may include a magnetism detector which detects magnetism of this magnet. Moreover, a magnet for use in capturing the magnetic particles, as described later, may also be utilized for origin detection. In the case where the substrate 100 for sample analysis is attachable to the turntable 201a only at a specific angle, the origin detector 203 may be omitted.

The rotation angle detection circuit 204 detects the angle of the shaft A of the motor 201. For example, the rotation angle detection circuit 204 may be a rotary encoder that is attached to the shaft A. In the case where the motor 201 is a brushless motor, the rotation angle detection circuit 204 may include a Hall generator that is provided on the brushless motor and a detection circuit which receives an output signal from the Hall generator and outputs the angle of the shaft A.

The drive circuit 206 rotates the motor 201. Specifically, based on an instruction from the control circuit 205, the substrate 100 for sample analysis is rotated clockwise or counterclockwise. Moreover, based on results of detection by the rotation angle detection circuit 204 and the origin detector 203 and on an instruction from the control circuit 205, stops swings or rotation of the substrate 100 for sample analysis.

The optical measurement unit 207 detects a signal (dye, luminescence, fluorescence, etc.) which is in accordance with the label substance 307 of the labeled antibody 308 that has bound to the composite 310 (FIG. 1) being retained on the substrate 100 for sample analysis.

The control circuit 205 is a CPU which is provided in the sample analysis device 200, for example. By executing a computer program that is loaded into a RAM (Random Access Memory; not shown), the control circuit 205 sends instructions to other circuitry in accordance with the procedure defined by the computer program. Upon receiving such an instruction, each circuit operates as will be described in the present specification, whereby the function of the respective circuit is realized. The instructions from the control circuit 205 are sent to the drive circuit 206, the rotation angle detection circuit 204, the optical measurement unit 207, and the like, as shown in FIG. 2A, for example. The procedure defined by the computer program is shown by a flowchart in the attached drawings.

Note that a RAM into which a computer program is loaded, i.e., a RAM storing a computer program, may be volatile or non-volatile. A volatile RAM is a RAM which in the absence of supplied power is unable to retain the information that is stored therein. For example, a dynamic random access memory (DRAM) is a typical volatile RAM. A non-volatile RAM is a RAM which is able to retain information without power being supplied thereto. For example, a magnetoresistive RAM (MRAM), a resistive random access memory (ReRAM), and a ferroelectric memory (FeRAM) are examples of non-volatile RAMs. In the present embodiment, a non-volatile RAM is preferably adopted. A volatile RAM and a non-volatile RAM are both examples of non-transitory, computer-readable storage media. Moreover, a magnetic storage medium such as a hard disk, and an optical storage medium such as an optical disc are also examples of non-transitory, computer-readable storage media. That is, a computer program according to the present disclosure may be recorded on various non-transitory computer-readable media, excluding any medium such as the atmospheric air (transitory media) that allows a computer program to be propagated as a radiowave signal.

In the present specification, the control circuit 205 is described as a distinct component element from the rotation angle detection circuit 204 and the origin detection circuit 203c of the origin detector 203. However, these may be implemented by the same hardware. For example, in a serial or parallel manner, a CPU (computer) which is provided in the sample analysis device 200 may execute a computer program to function as the control circuit 205, a computer program to function as the rotation angle detection circuit 204, and a computer program to function as the origin detection circuit 203c of the origin detector 203. This allows the CPU to apparently operate as distinct component elements.

(Substrate 100 for Sample Analysis)

Figure 3A:
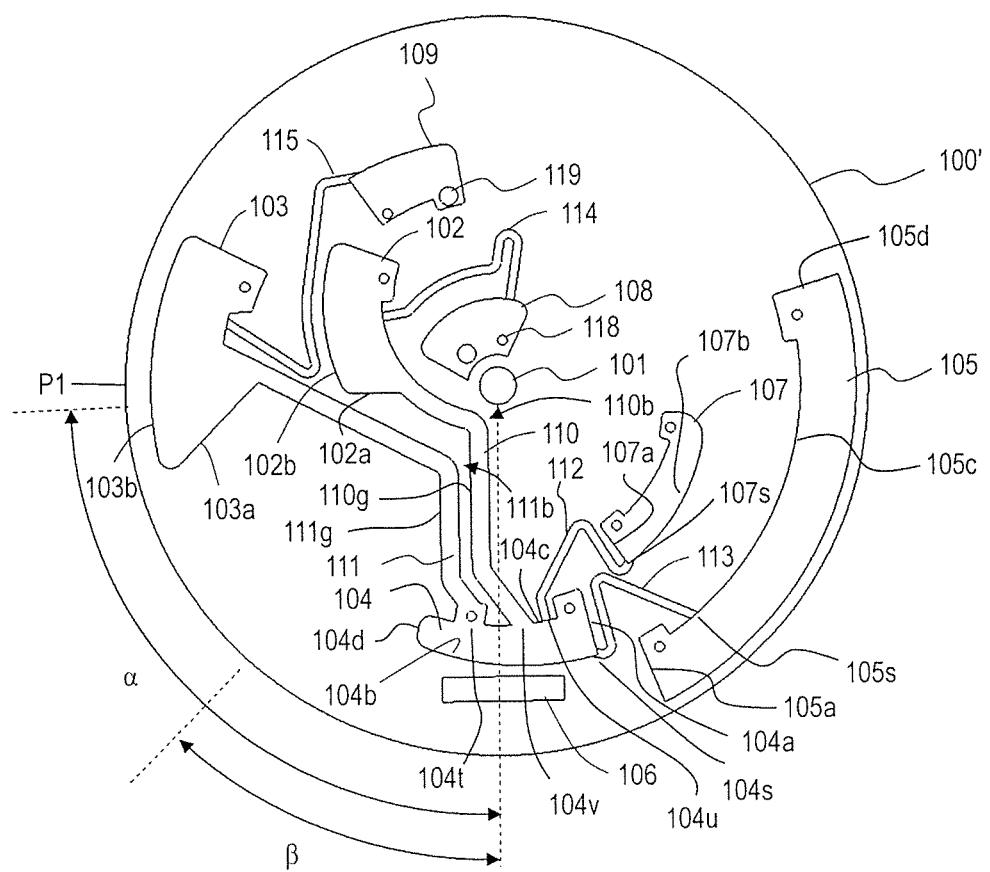
FIG. 3A An exemplary plan view of a substrate for sample analysis.
Figure 3B:
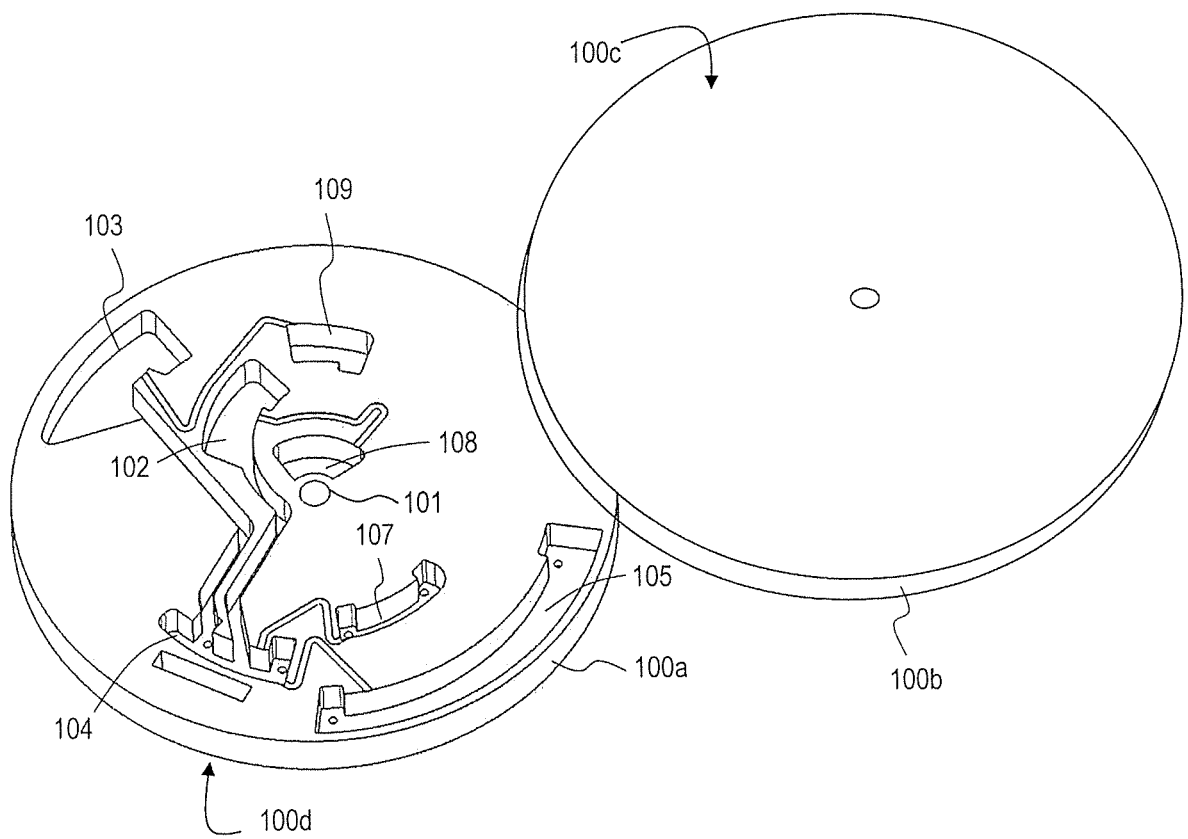
FIG. 3B An exemplary exploded perspective view of a substrate for sample analysis.

FIG. 3A and FIG. 3B are a plan view and an exploded perspective view of the substrate 100 for sample analysis. The substrate 100 for sample analysis includes a substrate 100' having a rotation axis 101 and a plate shape with a predetermined thickness along a direction which is parallel to the rotation axis 101. Although the substrate 100' of the substrate 100 for sample analysis has a circular shape in the present embodiment, it may alternatively be shaped as a polygon, an ellipse, a sector, or the like. The substrate 100' has two principal faces 100c and 100d. In the present embodiment, the principal face 100c and the principal face 100d are parallel to each other, and the thickness of the substrate 100' as defined by an interspace between the principal face 100c and the principal face 100d is constant irrespective of position within the substrate 100'. However, the principal faces 100c and 100d do not need to be parallel. For example, the two principal faces 100c and 100d may be partly non-parallel or parallel, or be entirely non-parallel. Moreover, at least one of the principal faces 100c and 100d of the substrate 100' may have a structure with recesses or protrusions. The substrate 100 for sample analysis includes a first chamber 102, a second chamber 103, a third chamber 104, a fourth chamber 105, a first storage chamber 108, a second storage chamber 109, and a reaction chamber 107, each located in the substrate 100'. Unless otherwise specified below, there is no particular limitation as to the shape of each chamber, which may have any arbitrary shape. Each chamber includes a space which is generally defined by an upper face and a lower face that are parallel to the two principal faces of the substrate 100' and three or more side faces located therebetween. Any two adjoining faces among the upper face, the lower face, and the side faces may not be parted by a clearly defined ridge. For example, the shape of each chamber may be an oblate sphere or a spheroid.

Furthermore, the substrate 100 for sample analysis includes a first channel 110, a second channel 111, a third channel 112, a fourth channel 113, a fifth channel 114, and a sixth channel 115, each located in the substrate 100'. The first channel 110 interconnects the first chamber 102 and the third chamber 104. The second channel 111 interconnects the second chamber 103 and the third chamber 104. The third channel 112 interconnects the reaction chamber 107 and the third chamber 104. The fourth channel 113 interconnects the third chamber 104 and the fourth chamber 105. The fifth channel 114 interconnects the first storage chamber 108 and the first chamber 102. The sixth channel 115 interconnects the second storage chamber 109 and the second chamber 103.

In the present embodiment, the substrate 100' of the substrate 100 for sample analysis is composed of a base substrate 100a and a cover substrate 100b. The respective spaces of the first chamber 102, the second chamber 103, the third chamber 104, the fourth chamber 105, the first storage chamber 108, the second storage chamber 109, and the reaction chamber 107 are formed within the base substrate 100a, and as the cover substrate 100b covers over the base substrate 100a, a top and a bottom of each space are created. In other words, these spaces are defined by inner surfaces of the substrate 100'. The first channel 110, the second channel 111, the third channel 112, the fourth channel 113, the fifth channel 114, and the sixth channel 115 are also formed in the base substrate 100a, and as the cover substrate 100b covers over the base substrate 100a, a top and a bottom of the respective channel space are created. In the present embodiment, the base substrate 100a and the cover substrate 100b are utilized respectively as an upper face and a lower face. The substrate 100' may be formed of a resin which may be acrylic, polycarbonate, polystyrene, or the like.

As has been described with reference to FIG. 1, the reaction chamber 107 is a reaction field in which the magnetic-particle-immobilized antibody 305, an analyte containing the antigen 306, and the labeled antibody 308 are allowed to react and form the composite 310. There is no particular limitation as to the shape of the reaction chamber 107.

Preferably, an end 107s of the third channel 112 that connects to the reaction chamber 107 is provided on, among side face portions of the reaction chamber 107, a side face portion 107b that is located at the outermost periphery side (i.e., away from the rotation axis 101). The reason is that, since the solution containing the composite 310 will rest against the side face portion 107b under a centrifugal force due to rotation of the substrate 100 for sample analysis, providing the end 107s of the third channel 112 at the side face portion 107b restrains the solution containing the composite 310 from being left without being transferred. Alternatively, however, it may be provided at a side face portion 107a adjacent to the side face portion 107b, at a position near the side face portion 107b. In the case where the end 107s is provided at the side face portion 107a, it is preferably provided at a position that encompasses the position of connection between the side face portion 107a and the side face portion 107b.

In the present embodiment, the substrate 100 for sample analysis includes the reaction chamber 107 as a reaction field where the composite 310 is allowed to form. Various means may be adopted in transferring the magnetic-particle-immobilized antibody 305, an analyte containing the antigen 306, and the labeled antibody 308 to the reaction chamber 107. For example, a mixed solution in which the magnetic-particle-immobilized antibody 305, the analyte containing the antigen 306, and the labeled antibody 308 have been previously mixed may be measured out, and the mixed solution may be injected into the reaction chamber 107 in the substrate 100 for sample analysis. Moreover, the substrate 100 for sample analysis may include chambers respectively retaining the magnetic-particle-immobilized antibody 305, the analyte containing the antigen 306, and the labeled antibody 308, and a channel (e.g., a capillary channel) via which each chamber and the reaction chamber 107 are coupled. In this case, the magnetic-particle-immobilized antibody 305, the analyte containing the antigen 306, and the labeled antibody 308 may be measured out into the respective chambers; the magnetic-particle-immobilized antibody 305, the analyte containing the antigen 306, and the labeled antibody 308 having been injected into the respective chambers may be transferred to the reaction chamber 107; and they may be mixed in the reaction chamber 107 to form the composite 310. Moreover, the magnetic-particle-immobilized antibody 305 and the labeled antibody 308 may be dried (hereinafter referred to as "dried reagents"). In this case, for example, the dried reagents may be retained in the reaction chamber 107, and dissolved by a liquid containing an analyte solution containing the antigen 306 to form the composite 310. Moreover, a dried reagent retained in a certain chamber during measurement may be dissolved by a predetermined solution, and an analyte solution containing the antigen 306 may be mixed in the reaction chamber 107, thereby allowing the composite 310 to form.

The solution containing the composite 310 is transferred to the third chamber 104 via the third channel 112.

In the third chamber 104, B/F separation is to be effected for the solution containing the composite 310. For this purpose, the substrate 100 for sample analysis includes a magnet 106. In the substrate 100 for sample analysis, the magnet 106 is located near the space of the third chamber 104. More specifically, the magnet 106 is disposed, among the four side faces of the third chamber 104, near the side face portion 104b that is the farthest from the rotation axis 101. However, the position of the magnet 106 in the substrate 100 for sample analysis may be at any position near the upper face or the lower face other than the side face portion 104b of the third chamber 104. In other words, so long as the magnetic particles can be captured by the magnet 106 onto the wall surface of the third chamber 104, there is no particular limitation as to its position. The magnet 106 may be configured to be capable of being attached or detached in adaptation with B/F separation, or undetachably attached to the substrate 100 for sample analysis.

Figure 3C:
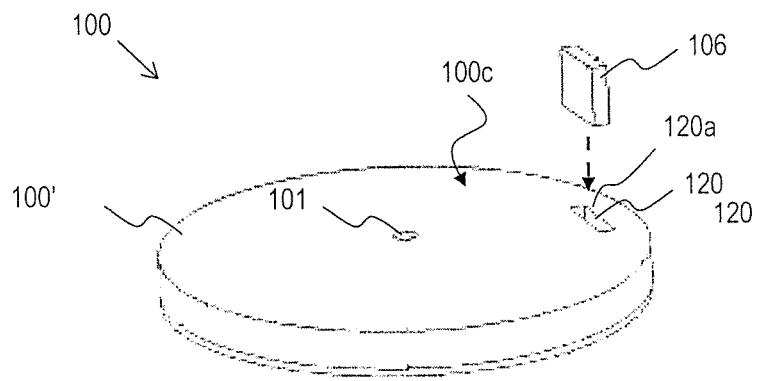
FIG. 3C A perspective view showing another exemplary structure of a substrate for sample analysis.

The magnet 106 may be provided on the sample analysis device 200. For example, the magnet 106 may be provided on the turntable 201a of the sample analysis device 200. In this case, the turntable 201a is preferably configured so that the substrate 100 for sample analysis can be placed thereon at a specific rotation angular position. As the user places the substrate 100 for sample analysis on the turntable 201a at a predetermined rotation angle, the magnet 106 becomes disposed at a position where it is able to capture the magnetic particles on the wall surface of the third chamber 104. The magnet 106 may be disposed on the turntable 201a of the sample analysis device 200 in a detachable manner. In this case, by removing the magnet 106 from the turntable 201a, the sample analysis device 200 becomes available also for any analysis for which B/F separation is unnecessary, or any substrate for sample analysis for which B/F separation is unnecessary. In the case where the magnet 106 is configured to be detachable, for example, the substrate 100' has a receptacle in which the magnet 106 can be accommodated. For example, as shown in FIG. 3C, the substrate 100' may have a dented receptacle 120 with an opening 120a in the principal face 100c. The receptacle 120 has a space in which the magnet 106 can be accommodated. By inserting the magnet 106 through the opening 120a into the receptacle 120, the magnet 106 becomes mounted to the substrate 100'. The opening 120a of the receptacle 120 may be made in the principal face 100d, or in a side face that is located between the two principal faces 100c and 100d.

There is no particular limitation as to the shape of the third chamber 104. Preferably, it is located more distant from the rotation axis 101 than is the reaction chamber 107. Preferably, an end 104s of the fourth channel 113 that connects to the third chamber 104 is provided on, among side face portions of the third chamber 104, a side face portion 104b that is located at the outermost periphery side (i.e., away from the rotation axis 101). The reason is that, since the wash solution or the like will rest against the side face portion 104b under a centrifugal force due to rotation of the substrate 100 for sample analysis, providing the end 104s of the fourth channel 113 at the side face portion 104b restrains the wash solution from being left without being transferred. Alternatively, however, it may be provided at a side face portion 104a adjacent to the side face portion 104b, at a position near the side face portion 104b. In the case where the end 104s is provided at the side face portion 104b, it is preferably provided at a position that encompasses the position of connection between the side face portion 104b and the side face portion 104a.

Moreover, an end 104v of the first channel 110, an end 104t of the second channel 111, and an end 104u of the third channel 112 that connect to the third chamber 104 are preferably provided on, among side face portions of the third chamber 104, a side face portion 104c that is located at the innermost periphery side (i.e., closest to the rotation axis 101), or at a position near the side face portion 104a or 104d adjacent to the side face portion 104c.

In the present embodiment, the first storage chamber 108 and the second storage chamber 109 hold a wash solution(s) which is used in the washing during B/F separation. As will be described in detail below, by transferring such wash solutions to the third chamber 104 at different points in time, the sample analysis system 501 of the present embodiment is able to wash the composite 310 multiple times at B/F separation. The liquids which are held in the first storage chamber 108 and the second storage chamber 109 will be referred to as a first wash solution and a second wash solution, respectively. The first wash solution and the second wash solution may be a wash solution of the same component, or wash solutions of different components. Moreover, the spaces of the first storage chamber 108 and the second storage chamber 109 may be of the same size or different sizes. Furthermore, the amounts of first wash solution and second wash solution that are held in the first storage chamber 108 and the second storage chamber 109 may be equal or different.

When the sample analysis system 501 is in use, the first wash solution and the second wash solution are introduced to the first storage chamber 108 and the second storage chamber 109, respectively. The present embodiment illustrates a construction where the first storage chamber 108 and the second storage chamber 109 are each provided. However, a construction may alternatively be adopted where these two storage chambers are composed as one; channels that connect respectively to the first chamber 102 and the second chamber 103 are provided in the storage chamber; and wash solutions are distributed to the first chamber 102 and the second chamber 103 via capillary action and rotation of the substrate 100 for sample analysis.

The first chamber 102 and the second chamber 103 retain the first wash solution and the second wash solution which were respectively held in the first storage chamber 108 and the second storage chamber 109. The first storage chamber 108 and the second storage chamber 109 are located closer to the rotation axis 101 than are the first chamber 102 and the second chamber 103, respectively.

The first chamber 102 and the second chamber 103 respectively house a first space and a second space. The first space and the second space are defined by inner surfaces of the substrate 100'. As shown in FIG. 3A, within the substrate, the substrate 100' includes a first side face 102a and a second side face 103a, which define a portion of the first space and the second space. These adjoin the first channel 110 and the second channel 111, respectively. In the example shown in FIG. 3A, as viewed from a direction which is parallel to the rotation axis 101, the first side face 102a and the second side face 103a are located on the same side with respect to the first space and the second space. In the example shown in FIG. 3A, as viewed from a direction which is parallel to the rotation axis 101, the first side face 102a and the second side face 103a are not parallel to each other. Moreover, in the example shown in FIG. 3A, the first side face 102a and the second side face 103a are planes which are parallel to the rotation axis 101.

Moreover, within the substrate 100', the substrate 100' includes a third side face 102b and a fourth side face 103b which define another portion of the first space and the second space. The third side face 102b and the fourth side face 103b respective adjoin the first side face 102a and the fourth side face 103b. The first side face 102a and the third side face 102b of the first space, as well as the second side face 103a and the fourth side face 103b of the second space, are the primary side faces that define the shape of a space among its plural side faces. Therefore, a tapered surface, a curved surface, or the like for smoothing out the corner (arris) may be provided between the first side face 102a and the third side face 102b. The same also applies to between the second side face 103a and the fourth side face 103b.

The transfer of liquids between the chambers by way of the channels can be attained by various methods. For example, a gravity-based transfer and a transfer based on a capillary force and a centrifugal force associated with rotation can be utilized. Hereinafter, these two transfer methods will be described in outline.

For example, the substrate 100 for sample analysis is supported so that its shaft A is tilted in a range which is greater than 0 degrees but not more than 90 degrees with respect to the vertical direction. Then, by changing the rotation angular position of the substrate 100 for sample analysis, the chamber from which the transfer occurs and in which a liquid exists is allowed to be disposed at a higher position than the chamber that is the destination of transfer. To be "high" means being located more upward along the vertical direction. As a result of this, the liquid can be transferred to the other chamber by utilizing gravity. In this case, the channel which couples between the chambers is not a capillary channel. A "capillary channel" would mean a channel with a narrow space which can be filled inside with a liquid via capillary action. A capillary channel may also be called a capillary tube.

Moreover, a capillary channel may also be utilized in transferring a liquid to another chamber. A liquid transfer through a capillary channel will be described with respect to an exemplary construction including chamber A and chamber B, which are not capillary tube spaces, and a capillary channel, which connects between chamber A and chamber B. When a liquid being retained in chamber A comes in contact with an opening that defines an interconnection between chamber A and the capillary channel, the liquid is pulled into the capillary channel by a capillary force, whereby the interior of the channel becomes filled with the liquid. However, when the substrate 100 for sample analysis is rotated with such a number of revolutions (including also a stopped state) as will apply to the liquid inside the channel a centrifugal force which is equal to or less than the capillary force that is acting on the liquid inside the channel, then the liquid in the capillary channel will remain in the capillary tube space, without being transferred to chamber B. In order to fill the interior of the capillary channel with the liquid thus via capillary action, an air hole (air pathway between the external environment and the chamber) must be provided at the chamber B side, i.e., at the outlet side of the capillary channel. Moreover, in order to effect a liquid transfer via capillary action within the closed space defined by chamber A, chamber B, and the capillary channel, an air hole must also be provided at the chamber A side, i.e., at the inlet side of the capillary channel, as dictated by the relationship between air pressures inside the chambers and the channel. Then, assuming that chamber B is disposed more distant from the rotation axis than is chamber A, from a state in which this capillary channel is filled with the liquid, the substrate 100 for sample analysis may be rotated with such a number of revolutions as will apply a centrifugal force which is greater than the capillary force that is acting on the liquid inside the capillary channel, whereby the liquid in chamber A can be transferred to chamber B with this centrifugal force.

In order to enhance the capillary force, a hydrophilic treatment may be performed for the inner surfaces of the substrate 100' defining the capillary channel, and for any inner surface near the interconnection between the capillary channel and each chamber. The hydrophilic treatment can be performed by coating the aforementioned inner surfaces with a nonionic-type, cation-type, anion-type, or amphoteric-type surfactant, performing a corona discharge treatment, or providing minute physical ruggednesses, and so on, for example (see Japanese Laid-Open Patent Publication No. 2007-3361, for example).

In the case where a liquid is to be transferred with a capillary force or a centrifugal force due to rotation, for example, a substrate 100 for sample analysis having a diameter of 60 mm can be rotated in a range from 100 rpm to 8000 rpm. The rotation speed is determined in accordance with the shape of each chamber and channel, the physical properties of liquids, the timing of transfers of liquids and treatments, and the like.

While supporting the substrate 100' so that the rotation axis 101 of the substrate 100' is inclined at an angle which is greater than 0° but not more than 90° with respect to the direction of gravity, the substrate 100' of the substrate 100 for sample analysis is retained at a predetermined rotation angle such that the third chamber 104 is situated below the first chamber 102 and the second chamber 103 along the direction of gravity. The angle of tilt of the rotation axis with respect to the direction of gravity is preferably 5° or more, more preferably not less than 10° and not more than 45°, and still more preferably not less than 20° and not more than 30°. In this case, the first chamber 102 forms a first recess with the first side face 102a and the third side face 102b, such that the first wash solution is retained in the first recess. Similarly, the second chamber 103 forms a second recess with the second side face 103a and the fourth side face 103b, such that the second wash solution is retained in the second recess. In the state shown in FIG. 3A, the first recess and the second recess are located on the same (right or left) side on the substrate 100', i.e., so as to be in one of the two regions divided by a straight line connecting the center of the third chamber 104 and the rotation axis 101. In other words, the dented shape of the first recess and second recess is oriented in a direction such that, when the substrate 100' is retained at a certain angle, a liquid(s) can be retained in both of the first recess and the second recess. In other words, the dented shape of the first recess and second recess is oriented in substantially the same direction.

In the example shown in FIG. 3A, when the substrate 100' of the substrate 100 for sample analysis is retained at a predetermined rotation angle such that the third chamber 104 is situated below the first chamber 102 and the second chamber 103 along the direction of gravity, the first side face 102a of the first chamber 102 and the second side face 103a of the second chamber 103 being not parallel makes it possible that, even when the entire amount of a wash solution that is retained in one of the chambers is moved therefrom to the third chamber 104 based on gravity, the other chamber is still able to retain at least a portion of its wash solution. Therefore, by appropriately selecting the rotation angle of the substrate 100 for sample analysis, wash solutions can be selectively transferred from the first chamber 102 and the second chamber 103 to the third chamber 104 at different points in time.

In the example shown in FIG. 3A, as viewed from a direction which is parallel to the rotation axis 101, an angle α constituted by the straight line connecting the center of the third chamber 104 and the rotation axis 101 and the first side face 102a is greater than an angle β constituted by the straight line connecting the center of the third chamber 104 and the rotation axis 101 and the second side face 103a. Therefore, if the substrate 100 for sample analysis is rotated clockwise from a rotation angle of the substrate 100 for sample analysis such that the first chamber 102 and the second chamber 103 are situated below the third chamber 104 along the direction of gravity (i.e., a rotation angle at which P1 indicated in FIG. 3A coincides with the 6 o'clock direction), the first side face 102a will be the first to become parallel (horizontal direction) to a direction which is orthogonal to the direction of gravity, whereby the entire amount of first wash solution in the first chamber 102 can be selectively transferred to the third chamber 104, after which the second wash solution retained in the second chamber 103 will be selectively transferred to the third chamber 104.

As described above, in the present embodiment, at a predetermined rotation angle, that is, while keeping the substrate 100 for sample analysis unrotating, the first wash solution and the second wash solution are selectively transferred from the first chamber 102 and the second chamber 103 to the third chamber 104. Therefore, the first channel 110 and the second channel 111 that connect the first chamber 102 and the second chamber 103 to the third chamber 104 are suitable for a transfer utilizing gravity, rather than a transfer utilizing capillary action and centrifugal force.

When making a transfer utilizing gravity, surface tension of the liquid may hinder a transfer of a wash solution to the first channel 110 or the second channel 111. In such cases, swinging the substrate 100', i.e., rotating it clockwise and counterclockwise within a predetermined angle range, can facilitate the transfer of each wash solution.

Specifically, the first channel 110 and the second channel 111 have such a large cross-sectional area that their interior will not be filled, via capillary action, respectively with the first wash solution and the second wash solution in the first chamber 102 and the second chamber 103. For example, in a cross section which is perpendicular to the direction that the channel extends, the first channel 110 and the second channel 111 have a width of about 1 mm or more and a depth of about 1 mm or more, and preferably a width of about 3 mm or more and a depth of about 3 mm or more.

In the example shown in FIG. 3A, the first channel 110 and the second channel 111 respectively have bent portions 110b and 111b; however, these bent portions may not be present. Preferably, the first channel 110 and the second channel 111 have side face portions 110g and 111g which are substantially parallel to the straight line connecting the center of the third chamber 104 and the rotation axis 101 (indicated by a broken line in FIG. 3A). Between the two regions as divided by the straight line connecting the center of the third chamber 104 and the rotation axis 101, the side face portions 110g and 111g are located in the same region as the first chamber 102 and the second chamber 103.

A first boundary position 116 exists upon the first side face 102a of the first chamber 102 or the side face composing the first channel 110, and a second boundary position 117 exists upon the second side face 103a of the second chamber 103 or the side face composing the second channel 111. More specifically, the first boundary position 116 and the second boundary position 117 are defined as follows, under conditions which do not take into account the influences of surface tension of the liquids retained in the first chamber 102 and the second chamber 103. First, while supporting the substrate 100' so that the rotation axis 101 of the substrate 100' is inclined at an angle which is greater than 0° but not more than 90° with respect to the direction of gravity, the substrate 100' of the substrate 100 for sample analysis is retained at a predetermined rotation angle such that the third chamber 104 is situated below the first chamber 102 and the second chamber 103 along the direction of gravity. The first boundary position 116 is defined by a boundary between the liquid surface of the first wash solution and the first channel 110 or the first side face 102a of the first chamber 102 that exists when, as the rotation angle of the substrate 100' is changed in one direction (e.g., clockwise in the example shown in FIG. 3A), the first wash solution in the first chamber 102 first begins to move toward the third chamber 104 at a position along the predetermined thickness direction. The second boundary position 117 is defined by a boundary between the liquid surface of the second wash solution and the second channel 111 or the second side face 103a of the second chamber 103 that exists when, as the rotation angle of the substrate 100' is changed in one direction (e.g., clockwise in the example shown in FIG. 3A), the second wash solution in the second chamber 103 first begins to move toward the third chamber 104 at a position along the predetermined thickness direction.

Figure 3D:
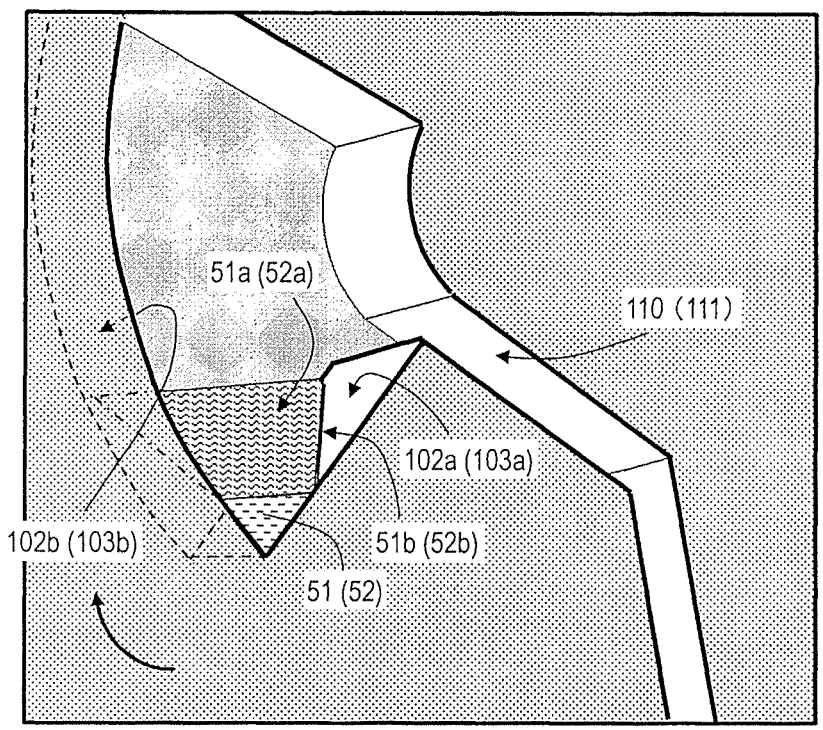
FIG. 3D A schematic perspective view showing an exemplary state in which a first wash solution is retained in a first chamber of a substrate for sample analysis.
Figure 3E:
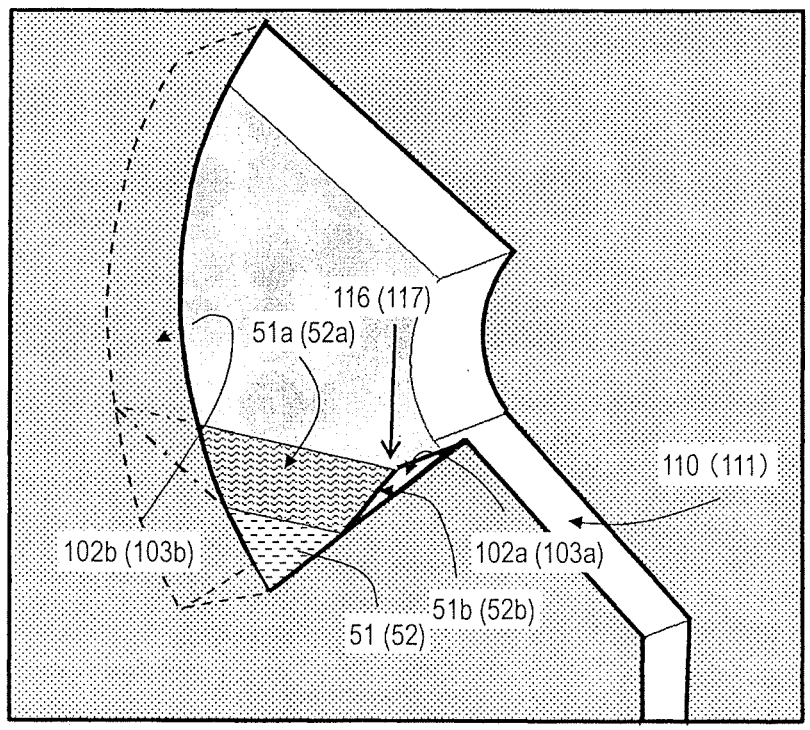
FIG. 3E A schematic perspective view showing an example of a first wash solution retained in a first chamber of a substrate for sample analysis and a first boundary position.
Figure 3F:
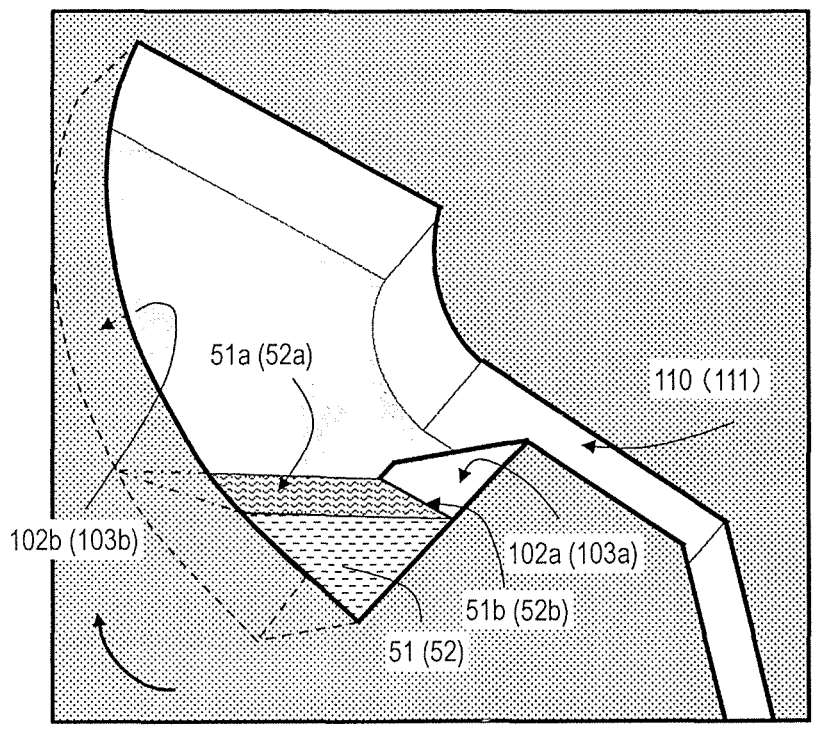
FIG. 3F A schematic perspective view showing another exemplary state in which a first wash solution is retained in a first chamber of a substrate for sample analysis.
Figure 3G:
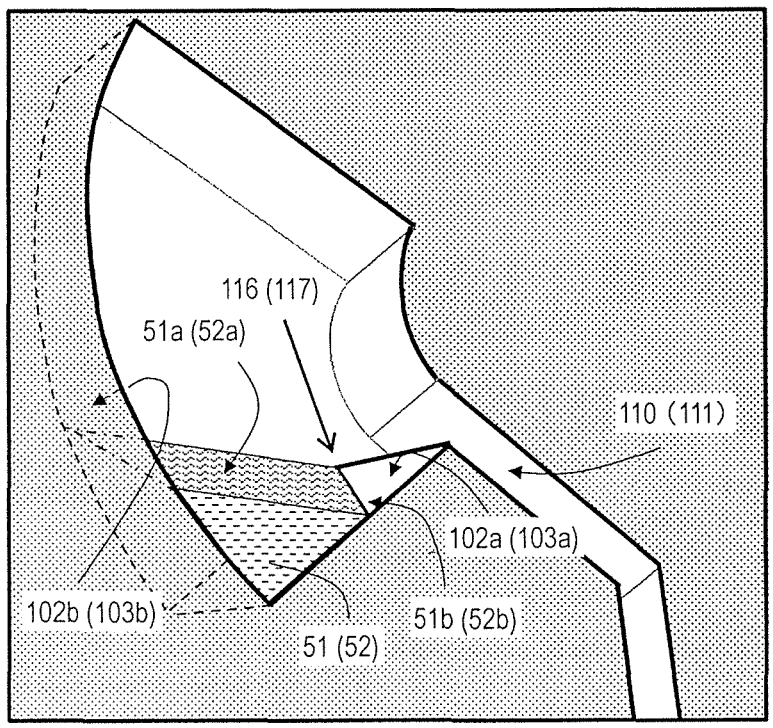
FIG. 3G A schematic perspective view showing another example of a first wash solution retained in a first chamber of a substrate for sample analysis and a first boundary position.

Hereinafter, this will be described more specifically with reference to the drawings. FIG. 3D and FIG. 3E are perspective views showing exemplary states of retaining the first wash solution 51 in the case where the first side face 102a and the third side face 102b of the first chamber 102 are parallel to the rotation axis 101 and the rotation axis 101 of the substrate 100' is retained at an inclination of 50° with respect to the direction of gravity. The first wash solution 51 is retained by the first side face 102a and the third side face 102b. When the substrate 100' is rotated from this state as indicated by an arrow in FIG. 3D, the first wash solution 51 will move within the first chamber 102 so that the liquid surface 51a of the first wash solution 51 maintains perpendicular to the direction of gravity. As a result, the position of the boundary 51b between the liquid surface 51a of the first wash solution 51 and the first side face 102a moves upon the first side face 102a. As shown in FIG. 3D, as the substrate 100' is further rotated, the boundary 51b between the liquid surface 51a of the first wash solution 51 and the first side face 102a reaches the opening of the first channel 110, and the first wash solution 51 first begins to move from the first channel 110 toward the third chamber 104. The position of the boundary 51b at this point is the first boundary position 116. As indicated by reference numerals in the parentheses in FIG. 3D and FIG. 3E. Similarly, the second boundary position 117 is defined with respect to the second wash solution 52 in the second chamber 103. FIG. 3F and FIG. 3G are, similarly, perspective views showing exemplary states of retaining the first wash solution 51 in the case where the first side face 102a of the first chamber 102 constitutes an angle of 30° with the rotation axis 101, the third side face 102b is parallel to the rotation axis 101, and the rotation axis 101 of the substrate 100' is retained at an inclination of 50° with respect to the direction of gravity.

Similarly, the first boundary position 116 and the second boundary position 117 are defined. Since the inclinations of the first side face 102a and the second side face 103a with respect to the rotation axis 101 and the amounts of first wash solution 51 and second wash solution differ, the first boundary position 116 and the second boundary position 117 are different between FIG. 3D and FIG. 3G. However, the rotation angle of the substrate 100' when the first wash solution 51 and the second wash solution 52 reach the first boundary position 116 and the second boundary position 117 can still be uniquely determined.

Therefore, the first chamber 102 and the second chamber 103 may be configured so that, in rotating the substrate 100', a rotation angle $\gamma 1$ at which the first wash solution in the first chamber 102 reaches the first boundary position 116 differs from a rotation angle $\gamma 2$ at which the second wash solution in the second chamber 103 reaches the second boundary position 117, whereby the respective wash solutions can be transferred to the third chamber 104 at different points in time.

The substrate 100 for sample analysis show in FIG. 3A is an example. Even if the positioning of the first chamber 102, the second chamber 103, the first channel 110, and the second channel 111 is altered, the first wash solution in the first chamber 102 and the second wash solution in the second chamber can be transferred to the third chamber 104 at different points in time. Other exemplary implementations of the substrate 100 for sample analysis will be described in detail below.

The third chamber 104 provides a place in which to effect B/F separation. From the reaction chamber 107, with a centrifugal force, a liquid containing the composite 310 and unreacted substance (hereinafter referred to as the reaction liquid) is transferred to the third chamber 104, via the third channel 112. For this reason, the third chamber 104 is located more distant from the rotation axis 101 than is the reaction chamber 107. Moreover, the first channel 110 and the second channel 111 need to be disposed so that, when the substrate 100' of the substrate 100 for sample analysis is retained at a predetermined rotation angle while supporting the substrate 100' so that the rotation axis 101 of the substrate 100' is inclined at an angle which is greater than 0° but not more than 90° with respect to the direction of gravity, the third chamber 104 is situated below the first chamber 102 (first boundary position 116) and/or the second chamber 103 (second boundary position 117). When the reaction liquid is transferred to the third chamber 104, the composite 310 and the unreacted magnetic-particle-immobilized antibody 305 in the reaction liquid (hereinafter, any allusion to both of these simultaneously will be made simply as the magnetic particles 311) are captured onto the side face portion 104b portion, by a magnetic force of the magnet 106 disposed near the side face portion 104b. Then, as the substrate 100 for sample analysis is rotated, a centrifugal force causes the reaction liquid (except for the magnetic particles containing any composite 310 that has been captured by the magnet 106 onto the side face 104 portion) to be transferred to the fourth chamber 105, via the fourth channel 113.

The fourth chamber 105 stores the liquid which is discharged with a centrifugal force from the third chamber 104 via the fourth channel 113. For this reason, the fourth chamber 105 is located more distant from the rotation axis 101 than is the third chamber 104.

Moreover, an end 105s of the fourth channel 113 that connects to the fourth chamber 105 is preferably provided on, among side face portions of the fourth chamber 105, a side face portion 105c that is located at the innermost periphery side (i.e., closest to the rotation axis 101), or at a position near the side face portion 105a or 105d adjacent to the side face portion 105c.

At least one air hole 118 is provided in each of the first chamber 102, the second chamber 103, the third chamber 104, the fourth chamber 105, the first storage chamber 108, the second storage chamber 109, and the reaction chamber 107. As a result, the interior of each chamber is maintained at the environmental air pressure, so that each channel can control the liquid to be moved or stopped by capillary action and the siphon principle. An opening 119 through which to inject or discharge liquids such as an analyte solution, a reaction solution, or a wash solution may be made in the first storage chamber 108, the second storage chamber 109, and the reaction chamber 107.

In each chamber, the air hole 118 and the opening 119 are preferably disposed on the upper face, toward the side face that is near the rotation axis 101. This restrains, even when the substrate 100 for sample analysis rotates with each chamber being filled with a liquid, the air hole 118 and the opening 119 from coming in contact with the liquid to allow the liquid to move through the air hole 118 and the opening 119 to outside of the substrate 100 for sample analysis. The air hole 118 and the opening 119 may be provided on a side face portion of each chamber.

Moreover, the space of each chamber preferably has a convex portion protruding toward the rotation axis 101, with the air hole 118 and opening 119 being located in this convex portion. Such construction will allow the air hole 118 and the opening 119 in each chamber to be positioned as close to the rotation axis 101 along the radial direction as possible. Thus, the amount of liquid that can be retained in each chamber without coming in contact with the air hole 108 and the opening 109 when the substrate 100 for sample analysis has rotated, within the chamber space, any dead space that is not available to retain a liquid can be reduced.

Next, with reference to FIG. 4, channels other than the first channel 110 and the second channel 111 will be described. The third channel 112, the fourth channel 113, the fifth channel 114, and the sixth channel 115 can be filled inside with a liquid via capillary action. Specifically, via capillary action, the third channel 112, the fourth channel 113, the fifth channel 114, and the sixth channel 115 can be filled inside with the liquids that are retained in the reaction chamber 107, the third chamber 104, the first storage chamber 108, and the second storage chamber 109, respectively. Each of these channels has, in a cross section which is perpendicular to the direction that the channel extends, a width of 5 mm or less and a depth of 50 μm to 300 μm, for example.

Moreover, it is preferable that the third channel 112, the fourth channel 113, the fifth channel 114, and the sixth channel 115 can control liquid movements by the siphon principle. For this reason, the third channel 112, the fourth channel 113, and the sixth channel 115 each have a first bent portion and a second bent portion. The first bent portion has a shape which is convex toward the opposite side from the rotation axis 101, whereas the second bent portion has a shape which is convex toward the rotation axis 101. Regarding two chambers that are connected by a channel, the first bent portion is located between the second bent portion and the chamber that is closer to the rotation axis 101.

Figure 4:
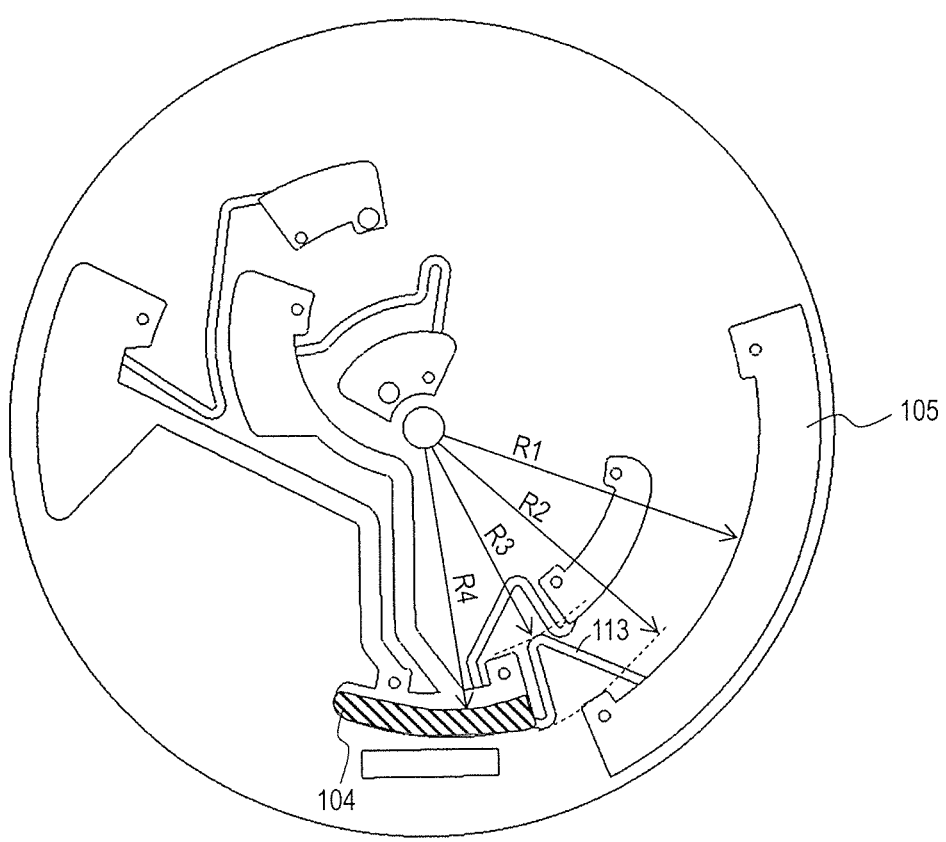
FIG. 4 A diagram showing an example of relative positioning between channels and chambers.

As shown in FIG. 4, given a distance R1 between the rotation axis 101 and the side face, which is closest to the rotation axis, of a chamber that is distant from the rotation axis 101, and given a distance R2 from the rotation axis 101 to a point on the first bent portion that is farthest from the rotation axis 101, it is preferable that R1>R2 be satisfied.

Moreover, when a liquid which is retained in a chamber that is close to the rotation axis 101 is retained concentratedly against a side face by a centrifugal force, given a distance R4 from the rotation axis 101 to the liquid surface of the liquid, and given a distance R3 from the rotation axis 101 to a point on the second bent portion that is nearest the rotation axis 101, it is preferable that R4>R3 be satisfied.

Although FIG. 4 takes the fourth channel 113 for example, the other channels also satisfy a similar relationship.

In transferring a reaction liquid by a centrifugal force from the reaction chamber 107 to the third chamber 104, the fourth channel 113 satisfying the aforementioned conditions can prevent the reaction liquid, which has been transferred to the third chamber 104, from being straightforwardly transferred to the fourth chamber 105. This point will be specifically described below.

As used herein, the siphon principle means the liquid transfer being controlled based on a balance between the centrifugal force acting on the liquid due to rotation of the substrate 100 for sample analysis and a capillary force within the channel. Specifically, an example where a liquid is transferred from the reaction chamber 107 to the third chamber 104, and further to the fourth chamber 104, will be described.

For example, in the case where the fourth channel 113 is a capillary channel which lacks siphon structure, in the course of a transfer from the reaction chamber 107 to the third chamber 104 via the third channel 112 based on a centrifugal force due to rotation of the substrate 100 for sample analysis, a liquid which has been transferred to the third chamber 104 will fill inside the fourth channel 113 because of a capillary force in the fourth channel 113. If rotation of the substrate 100 for sample analysis continues in this state, the liquid will not be retained in the third chamber 104, but will be transferred over to the fourth chamber 105 through the fourth channel 113. The rotation of the substrate 100 for sample analysis as referred to herein is based on a number of revolutions that allows a centrifugal force which is stronger than the capillary force in the fourth channel 113.

On the other hand, in the case where the fourth channel 113 has a siphon structure, with rotation of the substrate 100 for sample analysis, a liquid which has been transferred from the reaction chamber 107 to the third chamber 104 will be drawn into the fourth channel 113 by a capillary force in the fourth channel 113. However, if rotation of the substrate 100 for sample analysis continues with such a number of revolutions as will apply a centrifugal force which is stronger than the capillary force in the fourth channel 113, then the fourth channel 113 will not be entirely filled with the liquid, since the centrifugal force is stronger than the capillary force acting on the liquid. In other words, the liquid will fill the fourth channel 113 only up to the same height as the distance from the rotation axis 101 of the liquid surface of the liquid existing in the third chamber 104. Then, if it is desired to transfer the liquid in the third chamber 104 to the fourth chamber 105, rotation of the substrate 100 for sample analysis may be effected with such a number of revolutions (including also halted rotation) as will apply a centrifugal force which is weaker than the capillary force in the fourth channel 113, whereby the fourth channel 113 will become entirely filled with the liquid due to the capillary force. Thereafter, the substrate 100 for sample analysis may be rotated with such a number of revolutions as will apply a centrifugal force which is stronger than the capillary force in the fourth channel 113, whereupon the liquid in the third chamber 104 can be transferred to the fourth chamber 105.

Therefore, in the case where the liquid is to be transferred from the reaction chamber 107 to the third chamber 104 with the aforementioned number of revolutions, and the liquid is to be once retained in the third chamber 104 without allowing the liquid to be straightforwardly transferred to the fourth chamber 105, it is preferable that the fourth channel 113 be based on a siphon structure. The same also applies to the third channel 112, the fifth channel 114, and the sixth channel 115; however, a siphon structure may also be adopted even in the case where the aforementioned liquid control is not needed.

With further reference to the example of the fourth channel 113, the fourth channel 113 may be a capillary channel lacking siphon structure, or a channel utilizing gravity like the first channel 110 and the second channel 111.

In the course of transferring a liquid from the reaction chamber 107 to the fourth chamber 105 via the third chamber 104, if the liquid is to be once retained in the third chamber 104, given a fourth channel 113 which is a capillary channel lacking siphon structure, the following construction will be preferable. First, transfer of a liquid from the reaction chamber 107 to the third chamber 104 needs to be performed with such a number of revolutions (including also a stopped state) of the substrate 100 for sample analysis as will apply a centrifugal force which is equal to or less than a capillary force acting on the liquid filling the fourth channel 113. In this case, the third channel 112 is preferably a channel utilizing gravity. Moreover, inasmuch as the third channel 112 is a channel utilizing gravity, a recess similar to those of the first chamber 102 and the second chamber 103 is preferably provided for the side face portion 107b of the reaction chamber 107. In this case, transfer of the liquid from the reaction chamber 107 to the third chamber 104 is effected by changing the rotation angle of the substrate 100 for sample analysis so that the liquid which is retained in the recess of the side face portion 107b will move through the third channel 112 based on gravity.

On the other hand, in the course of transferring a liquid from the reaction chamber 107 to the fourth chamber 105 via the third chamber 104, if the liquid is to be once retained in the third chamber 104, given a fourth channel 113 which is a channel utilizing gravity, the following construction will be preferable. The third channel 112 may be either a capillary channel (including a siphon structure) or a channel utilizing gravity; however, in the case where the third channel 112 is a channel utilizing gravity, a recess similar to those of the first chamber 102 and the second chamber 103 is preferably provided for the side face portion 104b of the third chamber 104. In this case, transfer of the liquid from the third chamber 104 to the fourth chamber 105 is effected by changing the rotation angle of the substrate 100 for sample analysis, similarly to the case of transferring the liquid from the first chamber 102 (second chamber 103) to the third chamber 104.

As described above, the construction of the third channel 112, the fourth channel 113, the fifth channel 114, and the sixth channel 115 may be of various types.

The present embodiment illustrates that the third channel 112, the fourth channel 113, the fifth channel 114, and the sixth channel 115 are capillary channels, but the fifth channel 114 does not constitute a siphon. Alternatively, the fifth channel 114 may constitute a siphon. Moreover, the third channel 112 and the sixth channel 115 may not constitute siphons.

(Operation of the Sample Analysis System 501)

Figure 5:
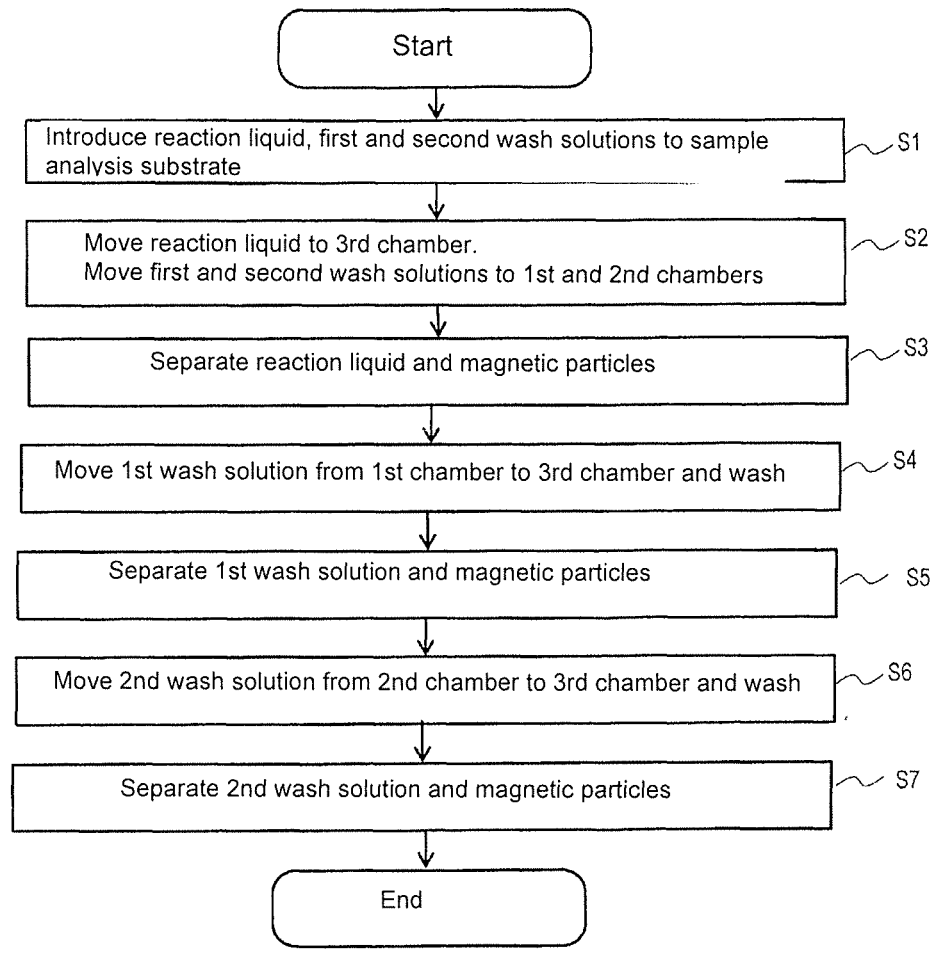
FIG. 5 A flowchart showing an exemplary operation of a sample analysis system.

An operation of the sample analysis system 501 will be described. FIG. 5 is a flowchart showing an operation of the sample analysis system 501. Prior to the following processes, the substrate 100 for sample analysis is mounted on the sample analysis device 200, and an origin of the substrate 100 for sample analysis is detected.

[Step S1]

Figure 6:
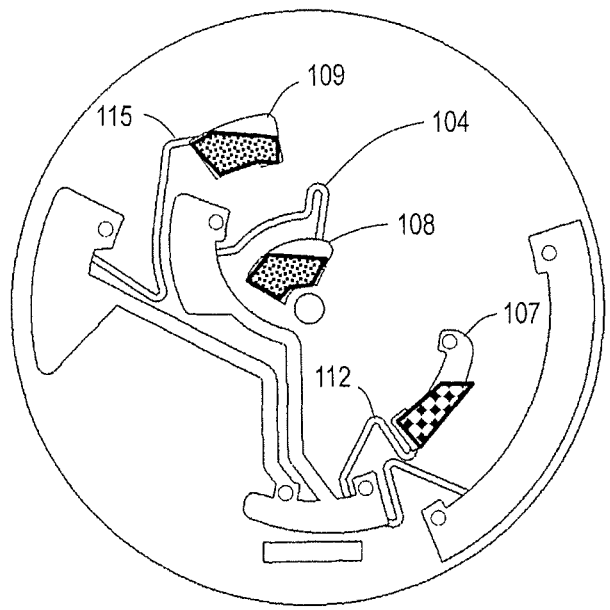
FIG. 6 A schematic diagram showing a stop angle of a substrate for sample analysis and liquid positions during operation of a sample analysis system.

First, as shown in FIG. 6, a first wash solution and a second wash solution are introduced to the first storage chamber 108 and the second storage chamber 109 of the substrate 100 for sample analysis. Also, the magnetic-particle-immobilized antibody 305, an analyte containing the antigen 306, and the labeled antibody 308 are introduced to the reaction chamber 107. For example, the reaction chamber 107 may retain a liquid containing the magnetic-particle-immobilized antibody 305, while chambers (not shown) that are provided in the substrate 100 for sample analysis may separately retain respective liquids containing the antigen 306 and the labeled antibody 308, and these may be transferred to the reaction chamber 107 with a centrifugal force due to rotation of the substrate 100 for sample analysis. In the reaction chamber 107, the magnetic-particle-immobilized antibody 305, the analyte containing the antigen 306, and the labeled antibody 308 are allowed to simultaneously react through antigen-antibody reactions, thus forming the composite 310. At this point, due to capillary action, the third channel 112, the fifth channel 114, and the sixth channel 115 are filled with the reaction liquid, the first wash solution, and the second wash solution, respectively.

[Step S2]

After the composite 310 is generated, the substrate 100 for sample analysis is rotated, thus moving the reaction liquid containing the composite 310 to the third chamber 104. At this point, the third channel 112 is filled with the reaction liquid due to capillary action. Therefore, as the rotation applies a centrifugal force which is stronger than the capillary force acting on the reaction liquid in the third channel 112 to the reaction involving the composite 310 in the reaction chamber 107, the reaction liquid is transferred to the third chamber 104. While the substrate 100 for sample analysis is rotating, the reaction liquid having been transferred to the third chamber 104 will not be transferred further to the fourth chamber 105. The reason is that, as described earlier, the fourth channel 113 constitutes a siphon; this prevents the liquid from moving through the fourth channel 113 in a direction toward the rotation axis 101 against the centrifugal force.

The rotation speed of the substrate 100 for sample analysis is set to a rate such that a centrifugal force occurring through rotation ensures that the reaction liquid and other liquids will not be moved based on gravity and that a centrifugal force which is stronger than the capillary force in each capillary channel will be applied. Hereinafter, for any rotation utilizing a centrifugal force, this rotation speed will be set.

At the same time that the reaction liquid moves, the first wash solution and the second wash solution are transferred from the first storage chamber 108 and the second storage chamber 109, through the fifth channel 114 and the sixth channel 115, to the first chamber 102 and the second chamber 103.

Figure 7:
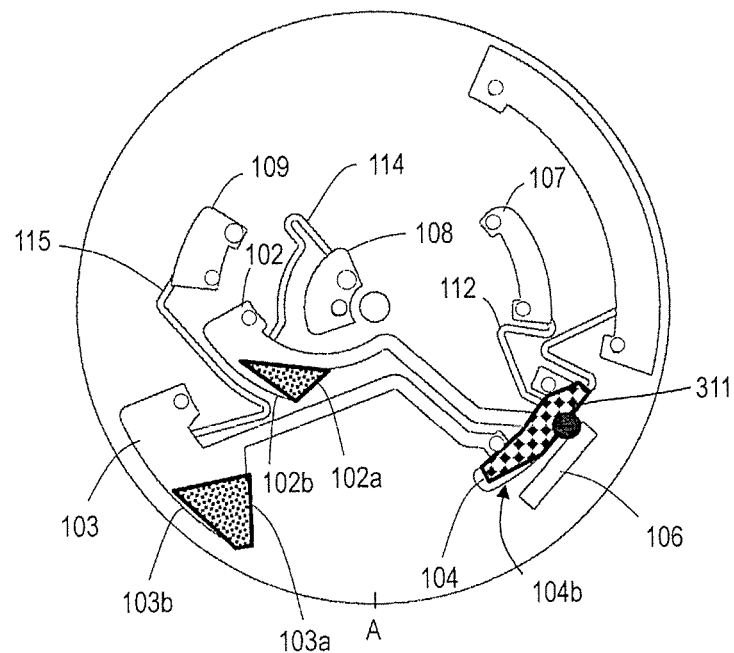
FIG. 7 A schematic diagram showing a stop angle of a substrate for sample analysis and liquid positions during operation of a sample analysis system.

After the reaction liquid and the wash solutions are entirely transferred, respectively to the second chamber 103 and the first chamber 102, the substrate 100 for sample analysis is stopped at a predetermined angle. As shown in FIG. 7, for example, the predetermined angle is an angle A at which the first wash solution and the second wash solution do not flow out of the first chamber 102 and the second chamber 103. The angle A is smaller than the rotation angle γ1 at which the first wash solution in the first chamber 102 would reach the first boundary position 116. Hereinafter, for ease of understanding, as shown in FIG. 7, in a substrate 100 for sample analysis which is retained so that the rotation axis 101 is inclined at an angle θ from the direction of gravity, any angle of the substrate 100 for sample analysis will be represented relative to the vertical direction of the rotation axis 101. At this point, the fourth channel 113 is filled with the reaction liquid due to capillary action.

[Step S3]

When the reaction liquid containing the magnetic particles 311 is transferred into the third chamber 104, the magnetic particles 311 containing the composite 310 in the reaction liquid are captured by the magnet 106 onto the side face portion 104b portion. Thereafter, the substrate 100 for sample analysis is rotated. A centrifugal force occurs with the rotation, this centrifugal force acting on the liquid and the magnetic particles 311 in the direction of the side face portion 104b of the third chamber 104, as shown in FIG. 7. The direction in which the centrifugal force acts is identical to the direction of the attractive force that the magnetic particles 311 receive from the magnet 106. Therefore, the magnetic particles 311 are strongly pressed against the side face portion 104b.

Under the centrifugal force, the reaction liquid is discharged from the fourth channel 113, and transferred to the fourth chamber 105. With a sum of the centrifugal force and the attractive force of the magnet 106, the magnetic particles 311 are strongly pressed against the side face portion 104b, and captured. As a result, only the reaction liquid is discharged from the second channel 111, while the magnetic particles 311 remain in the third chamber 104.

On the other hand, during rotation of the substrate 100 for sample analysis, the first wash solution and the second wash solution which are retained in the first chamber 102 and the second chamber 103 move to side face portions which are farther away from the rotation axis 101, including respectively the third side face 102b and the fourth side face 103b, due to centrifugal force. In other words, the first wash solution and the second wash solution move to side face portions which are farther away from the rotation axis 101 due to centrifugal force. Therefore, there occurs essentially no transfer of the first wash solution and the second wash solution to the third chamber due to rotation of the substrate 100' at step S3.

Figure 8:
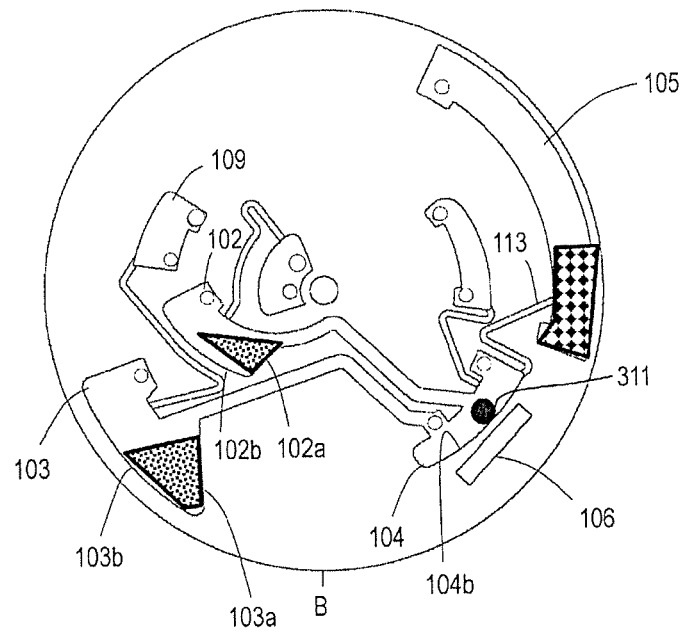
FIG. 8 A schematic diagram showing a stop angle of a substrate for sample analysis and liquid positions during operation of a sample analysis system.

As shown in FIG. 8, after the liquid has all moved to the fourth chamber 105, for example, rotation of the substrate 100 for sample analysis is stopped at an angle B. The angle B is smaller than the rotation angle γ1 at which the first wash solution in the first chamber 102 would reach the first boundary position 116. As a result, the reaction liquid and the magnetic particles 311 become separated. Specifically, the reaction liquid moves to the fourth chamber 105 while the magnetic particles 311 remain in the third chamber 104. The angle B is an angle at which the first wash solution and the second wash solution do not flow out of the first chamber 102 and the second chamber 103. The angle B may be equal to or different from the angle A. Note that the angle at which the first wash solution and the second wash solution do not flow out of the first chamber 102 and the second chamber 103 also depends on the amounts of first wash solution and second wash solution that are retained in the first chamber 102 and the second chamber 103.

As shown in FIG. 8, in this state, the first chamber 102 retains the entire amount of first wash solution with the first side face 102a and the third side face 102b. Similarly, the second chamber 103 retains the entire amount of second wash solution with the second side face 103a and the fourth side face 103b.

Hereinafter, in explaining the rotation angle of the substrate 100 for sample analysis for transferring the first wash solution and the second wash solution from the first chamber 102 and the second chamber 103, the rotation angle of the substrate 100 for sample analysis in this state will be referred to as the reference angle.

[Step S4 (Process (a))]

Figure 9:
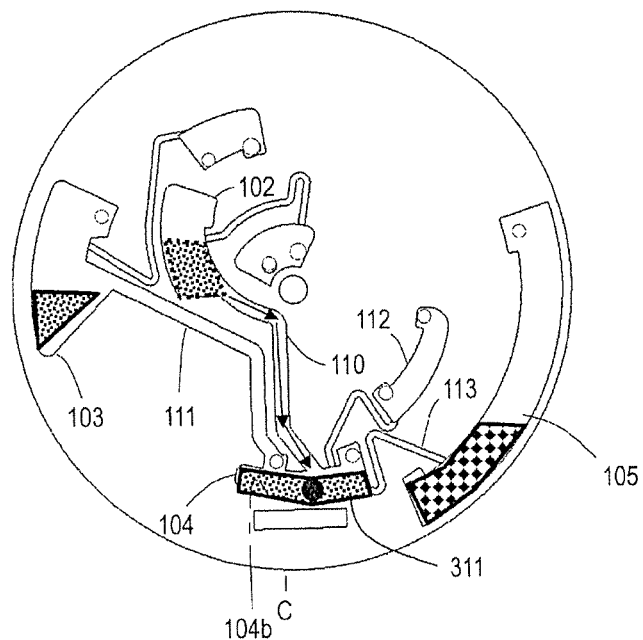
FIG. 9 A schematic diagram showing a stop angle of a substrate for sample analysis and liquid positions during operation of a sample analysis system.

As shown in FIG. 9, the substrate 100 for sample analysis is rotated clockwise from the reference angle by a rotation angle A1, and stopped at an angle C (first angle). As a result, the first wash solution in the first chamber 102 is transferred through the first channel 110 to the third chamber 104 based on gravity. The angle C is greater than the rotation angle γ1 at which the first wash solution in the first chamber 102 would reach the first boundary position 116, and smaller than the rotation angle γ2 at which the second wash solution in the second chamber 103 would reach the second boundary position 117. At this point, the second wash solution of the second chamber 103 is still retained in the second chamber 103.

At this time, the entire amount of first wash solution retained in the first chamber 102 is transferred to the third chamber 104. The amount of second wash solution to be transferred from the second chamber 103 to the third chamber 104 is zero. Moreover, a portion of the first wash solution in the third chamber 104 moves to the fourth channel 113 via capillary action.

In order to surely transfer the entire amount of first wash solution to the third chamber 104, clockwise and counterclockwise rotations may be alternated to about several degrees around the angle C, i.e., swung. The angle C may be an angle at which the first wash solution is transferred from the first chamber 102 to the third chamber 104 based on gravity but at which the second wash solution is not transferred from the second chamber 103 to the third chamber 104.

[Step S5 (Process (c))]

Figure 10:
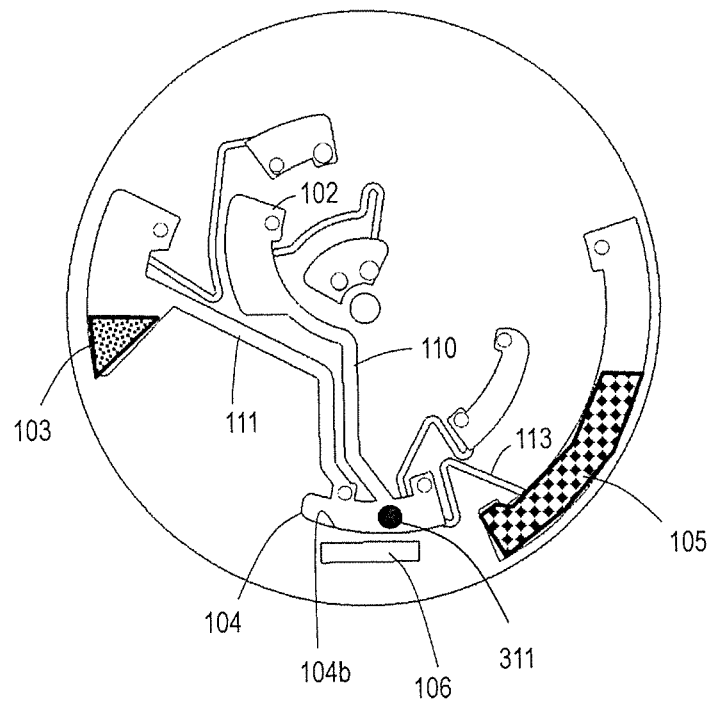
FIG. 10 A schematic diagram showing a stop angle of a substrate for sample analysis and liquid positions during operation of a sample analysis system.

Even if the first wash solution is transferred into the third chamber 104, the magnetic particles 311 remain captured by the magnet 106 onto the side face portion 104b. Thereafter, the substrate 100 for sample analysis is rotated. A centrifugal force occurs with rotation, whereby the first wash solution in the third chamber 104 is transferred through the fourth channel 113 to the fourth chamber 105. With a sum of the centrifugal force and the attractive force of the magnet 106, the magnetic particles 311 are strongly pressed against the side face portion 104b and captured. Therefore, as shown in FIG. 10, only the first wash solution is discharged from the third chamber 104, while the magnetic particles 311 remain in the third chamber 104.

On the other hand, during rotation of the substrate 100', the second wash solution retained in the second chamber 103 moves to the side face portion which is farther away from the rotation axis 101, including the fourth side face 103b, due to centrifugal force. Therefore, there occurs essentially no transfer of the second wash solution to the third chamber due to rotation of the substrate 100' at step S5.

[Step S6 (Process (b))]

Figure 11:
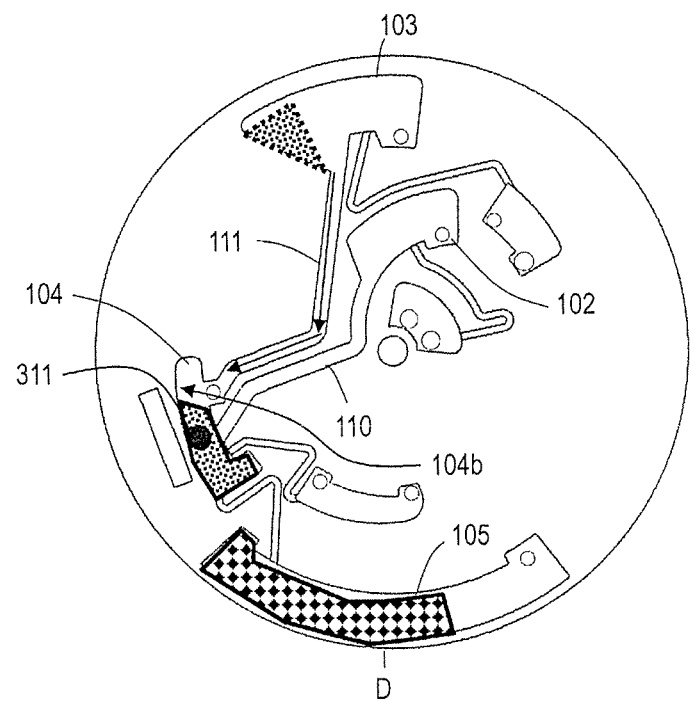
FIG. 11 A schematic diagram showing a stop angle of a substrate for sample analysis and liquid positions during operation of a sample analysis system.

As shown in FIG. 11, the substrate 100 for sample analysis is stopped at an angle D (second angle). This angle D is an angle that is reached as the substrate is rotated clockwise from the reference angle by the rotation angle of A1 and further rotated clockwise by a rotation angle of A2. The angle D is greater than the rotation angle γ2 at which the second wash solution in the second chamber 103 would reach the second boundary position 117.

Note that, beginning from the rotation state in step S5, if the rotation speed is decreased so that the substrate 100 for sample analysis is directly stopped at an angle D (second angle), the liquid surface of the second wash solution retained in the second chamber 103 may become so turbulent that it is unsuitable for transfer of the second wash solution. In this case, from the rotation state of step S5, the rotation speed may be decreased in order to temporarily stop the substrate 100 for sample analysis at the angle C (second angle), and thereafter the substrate 100 for sample analysis may be rotated clockwise by the rotation angle of A2, and stopped at the angle D.

As a result, the second wash solution in the second chamber 103 is transferred through the second channel 111 to the third chamber 104 based on gravity. At this time, since no first wash solution remains in the first chamber 102, there is no liquid movement from the first chamber 102 to the third chamber 104.

At this time, the entire amount of second wash solution that is retained in the second chamber 103 is transferred to the third chamber 104. The amount of first wash solution to be transferred from the first chamber 102 to the third chamber 104 is zero. Moreover, a portion of the second wash solution in the third chamber 104 moves to the fourth channel 113 via capillary action.

In order to surely transfer the entire amount of second wash solution to the third chamber 104, clockwise and counterclockwise rotations may be alternated to about several degrees around the angle D, i.e., swung. The angle D may be an angle at which the second wash solution is able to be transferred from the second chamber 103 to the third chamber 104 based on gravity.

[Step S7 (Process (b))]

Figure 12:
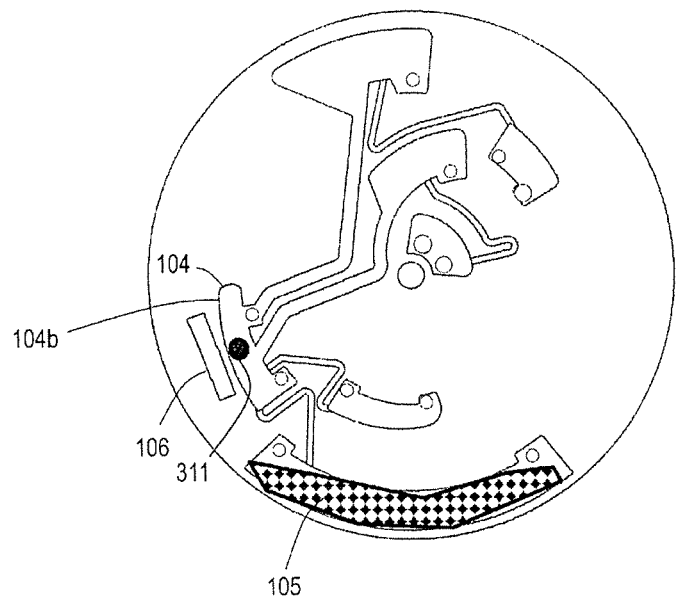
FIG. 12 A schematic diagram showing a stop angle of a substrate for sample analysis and liquid positions during operation of a sample analysis system.

Even if the second wash solution is transferred into the third chamber 104, the magnetic particles 311 remain captured by the magnet 106 onto the side face portion 104b portion. Thereafter, the substrate 100 for sample analysis is rotated. A centrifugal force occurs with rotation, whereby the second wash solution in the third chamber 104 is transferred through the fourth channel 113 to the fourth chamber 105. With a sum of the centrifugal force and the attractive force of the magnet 106, the magnetic particles 311 are strongly pressed against the side face portion 104b and captured. Therefore, as shown in FIG. 12, only the second wash solution is discharged from the third chamber 104, while the magnetic particles 311 remain in the third chamber 104. That is, B/F separation takes place.

Through the above processes, B/F separation, or specifically, a separation between the magnetic particles 311 and various unreacted substances occurs.

Thereafter, a reagent for effecting signal detection is introduced to the third chamber 104, and the optical measurement unit 207 is used to detect dye, luminescence, fluorescence, or other signals which are in accordance with the label substance 307 of the labeled antibody 308 having been bound to the composite 310 contained in the magnetic particles 311. Thus, it is possible to achieve detection of the antigen 306, quantification of the concentration of the antigen 306, and so on.

Thus, with a substrate for sample analysis, a sample analysis device, a sample analysis system, and a program for sample analysis according to the present embodiment, liquids which are retained in a plurality of different chambers can be introduced to separate chambers at different points in time. Therefore, when the substrate for sample analysis is used in effecting B/F separation, a sufficient washing effect can be attained by performing multiple times of washing. Moreover, this operation can be realized through control of the rotation and stopping of the substrate for sample analysis, and control of the stopping angles. Hence, without involving the use of a large-sized analysis apparatus or manual maneuvering by an operator, they are suitably applicable to assay techniques that carry out analysis of components within an analyte through complicated reaction steps, including B/F separation.

Other Embodiments

The above embodiment illustrates an example of washing in B/F separation. However, a substrate for sample analysis, a sample analysis device, a sample analysis system, and a program for sample analysis according to the present embodiment are applicable to various methods of sample analysis for introducing solutions that are not wash solutions to the same chamber over multiple times as described above.

Although introduction of liquids to chambers is performed in consecutive manners in the above embodiment, appropriate control of rotation and stop of the substrate for sample analysis and appropriate control of the stopping angle would make it possible to include other processes in between.

Moreover, at step S4 in the present embodiment, the entire amount of first wash solution retained in the first chamber 102 is transferred to the third chamber 104, but the second wash solution retained in the second chamber 103 is not transferred to the third chamber 104. Moreover, the entire amount of second wash solution retained in the second chamber 103 is transferred to the third chamber 104 at step S6. However, the substrate for sample analysis, sample analysis device, sample analysis system, and program for sample analysis according to the present disclosure are not limited to such implementation. For example, at step S4, a first predetermined amount of first wash solution retained in the first chamber 102 and a second predetermined amount of second wash solution retained in the second chamber 103 may be transferred to the third chamber 104, and at step S6, a third predetermined amount of first wash solution retained in the first chamber 102 and a fourth predetermined amount of second wash solution retained in the second chamber 103 may be transferred to the third chamber 104. In other words, at step S4 and/or step S6, the first wash solution and the second wash solution may be transferred to the third chamber 104 by each predetermined amount.

Figure 13A:
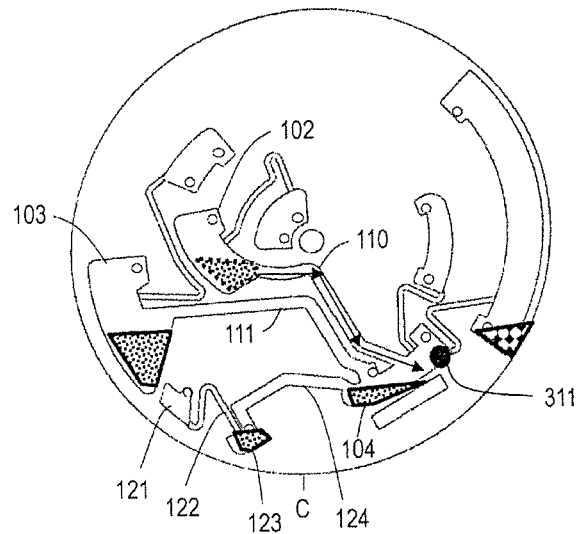
FIG. 13A A schematic diagram showing an example of a stop angle of a substrate for sample analysis and liquid positions during operation of a sample analysis system, in the case where another mode of a substrate for sample analysis is used.

Although the substrate for sample analysis in the above embodiment includes two chambers to retain wash solutions, it may include three or more chambers. FIG. 13 shows an example of a substrate for sample analysis which includes three chambers to retain wash solutions. As shown in FIG. 13A, in addition to the construction shown in FIG. 3, the substrate for sample analysis includes a third storage chamber 121, a fifth chamber 123, a seventh channel 122, and an eighth channel 124. The seventh channel 122 connects the third storage chamber 121 and the fifth chamber 123, while the eighth channel 124 connects the fifth chamber 123 and the third chamber 104. Similarly to the sixth channel 115, the seventh channel 122 is able to transfer liquid via capillary action, and constitutes a siphon. Similarly to the first channel 110, the seventh channel 122 is configured to be capable of transferring liquid based on gravity. The third storage chamber 121 retains the third wash solution.

In the case of using the substrate for sample analysis shown in FIG. 13A, the above procedure of maneuvering is also possible. First, at the aforementioned step S1, the third wash solution is further introduced to the third storage chamber 121. At step S2, the third wash solution in the third storage chamber 121 is transferred to the fifth chamber 123, similarly to other wash solutions.

Figure 13B:
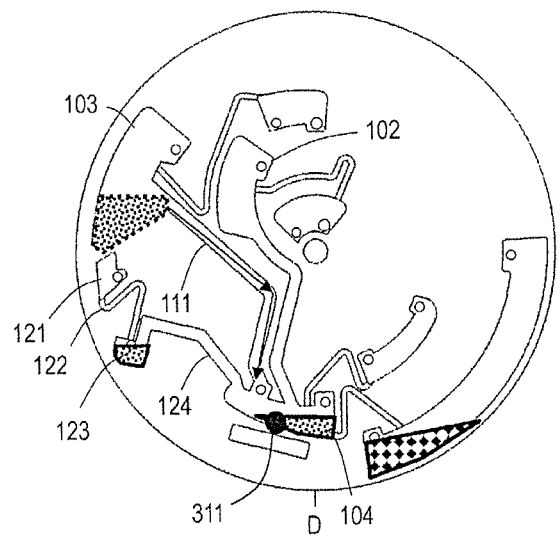
FIG. 13B A schematic diagram showing an example of a stop angle of a substrate for sample analysis and liquid positions during operation of a sample analysis system, in the case where another mode of a substrate for sample analysis is used.

Thereafter, step S3 to step S7 are carried out to, as shown in FIG. 13A and FIG. 13B, move the first wash solution and the second wash solution from the first chamber 102 and the second chamber 103 to the third chamber 104 at the angle C and the angle D, respectively.

Figure 13C:
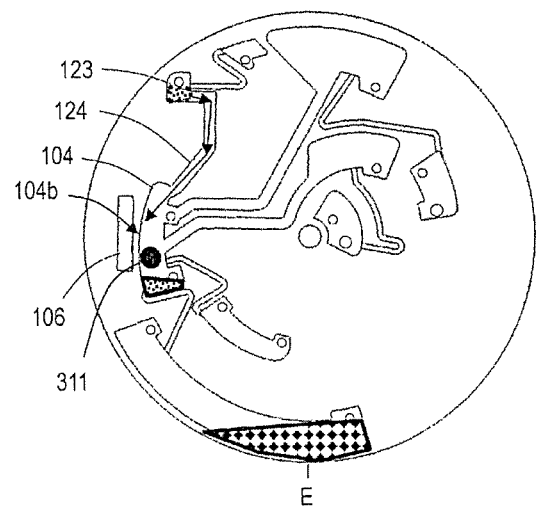
FIG. 13C A schematic diagram showing an example of a stop angle of a substrate for sample analysis and liquid positions during operation of a sample analysis system, in the case where another mode of a substrate for sample analysis is used.

After step S7, as shown in FIG. 13C, the substrate 100 for sample analysis is stopped at an angle E (third angle). This angle E is an angle that is reached as the substrate is rotated clockwise from the reference angle by the rotation angles of A1 and A2 and further rotated clockwise by the rotation angle of A3.

As a result, the third wash solution in the fifth chamber 123 is transferred through the eighth channel 124 to the third chamber 104 based on gravity. At this time, since no first wash solution and no second wash solution remain in the first chamber 102 and the second chamber 103, there is no liquid movement from the first chamber 102 and the second chamber 103 to the third chamber 104.

As a result, the entire amount of third wash solution retained in the fifth chamber 123 is transferred to the third chamber 104. The amounts of first wash solution and second wash solution to be transferred from the first chamber 102 and the second chamber 103 to the third chamber 104 are each zero. At this time, a portion of the third wash solution in the third chamber 104 moves to the fourth channel 113 via capillary action.

Even if the third wash solution is transferred into the third chamber 104, the magnetic particles 311 remain captured by the magnet 106 onto the side face portion 104b. Thereafter, the substrate 100 for sample analysis is rotated. A centrifugal force occurs with rotation, whereby the third wash solution in the third chamber 104 is transferred through the fourth channel 113 to the fourth chamber 105. With a sum of the centrifugal force and the attractive force of the magnet 106, the magnetic particles 311 are strongly pressed against the side face portion 104b and captured. Therefore, as shown in FIG. 12, only the second wash solution is discharged from the third chamber 104, while the magnetic particles 311 remain in the third chamber 104.

Moreover, by using the substrate for sample analysis shown in FIG. 13A, a liquid which is not a wash solution may be retained in either the first chamber 102, the second chamber 103, or the fifth chamber 123. For example, the first wash solution and the second wash solution may be respectively retained in the first chamber 102 and the second chamber 103, while a reagent solution for effecting signal detection, e.g., coloring, a luminescence reagent, etc., may be retained in the fifth chamber 123. In this case, by using the above-described procedure, after two times of washing with the first wash solution and the second wash solution are finished, the reagent solution for effecting signal detection retained in the fifth chamber 123 may be transferred to the third chamber 104 to detect a signal from the labeled antibody occurring in the third chamber 104.

Although the present embodiment has described an example of performing a sample analysis by using magnetic particles, the substrate for sample analysis, sample analysis device, sample analysis system, and program for a sample analysis system according to the present disclosure are not limited to a sample analysis by using magnetic particles. For example, rather than magnetic particles, it may be a wall surface within the chamber that the primary antibody is immobilized to.

Specifically, in the case where the chamber is composed of a material such as polystyrene or polycarbonate, the primary antibody can be immobilized to a wall surface within the chamber through physisorption. Moreover, a functional group such as an amino group or a carboxyl group may be carried on the chamber wall surface, and a primary antibody may be immobilized to the wall surface within the chamber via a chemical bond. As a result, a sandwiched type of combination reaction with the antigen or the labeled antibody can be effected within the chamber. Moreover, a metal substrate may be provided on the wall surface within the chamber, and the primary antibody may be allowed to bind to the metal substrate by using a SAM, thereby immobilizing the primary antibody. As a result, a sandwiched type of combination reaction with the antigen or the labeled antibody can be effected within the chamber.

The implementation which immobilizes the primary antibody to the wall surface in the chamber through physisorption can be used in a measurement system which detects a dye, chemiluminescence, or fluorescence signal, for example. On the other hand, the implementation which immobilizes the primary antibody to a metal substrate can be used in a measurement system which detects mainly an electrochemical signal (e.g., an electric current) or an electrochemiluminescence signal as the signal.

In these cases, the magnet 106 shown in FIG. 3 is unnecessary. Moreover, the reaction field in which to form the composite 310 is not the reaction chamber 107 but the third chamber 104. Therefore, the primary antibody is immobilized to the wall surface of the third chamber 104. Moreover, the substrate for sample analysis, sample analysis device, sample analysis system, and program for a sample analysis system according to the present disclosure are applicable to not only non-competitive assays (sandwich immunoassay) but also competitive assays and genetic detection techniques based on hybridization.

(Other Example Implementations of the Substrate 100 for Sample Analysis)

Hereinafter, other example implementations of the substrate 100 for sample analysis will be described. FIGS. 14A, 14B, 14C through FIGS. 18A, 18B, 18C show other exemplary constructions for the first chamber 102, the second chamber 103, the first channel 110, and the second channel 111 of the substrate 100 for sample analysis. For ease of understanding, these figures only show the rotation axis 101, the first chamber 102, the second chamber 103, the third chamber 104, the first channel 110, and the second channel 111 of the substrate 100' of the substrate 100 for sample analysis.

In a first example, in the first chamber 102, the first boundary position 116 is closer to the rotation axis 101 than is the first side face 102a; and in the second chamber 103, the second boundary position 117 is closer to the rotation axis 101 than is the second side face 103a. The substrate 100' is supported so that the rotation axis 101 is inclined at an angle which is greater than 0° but not more than 90° with respect to the direction of gravity, and retained at an arbitrary predetermined reference angle at which the first wash solution and the second wash solution retained in the first chamber 102 and the second chamber 103 are not transferred to the third chamber 104 via the first channel 110 and the second channel 111, respectively. When the substrate 100' in this state is viewed from a direction which is parallel to the rotation axis 101, in the first example, the first boundary position 116 and the second boundary position 117 are on either the right or left side on the substrate 100', i.e., in one of the two regions divided by a straight line connecting the central neighborhood of the third chamber 104 and the rotation axis 101. The substrate 100' shown in FIG. 3A falls into the category of the first example.

Figure 14A:
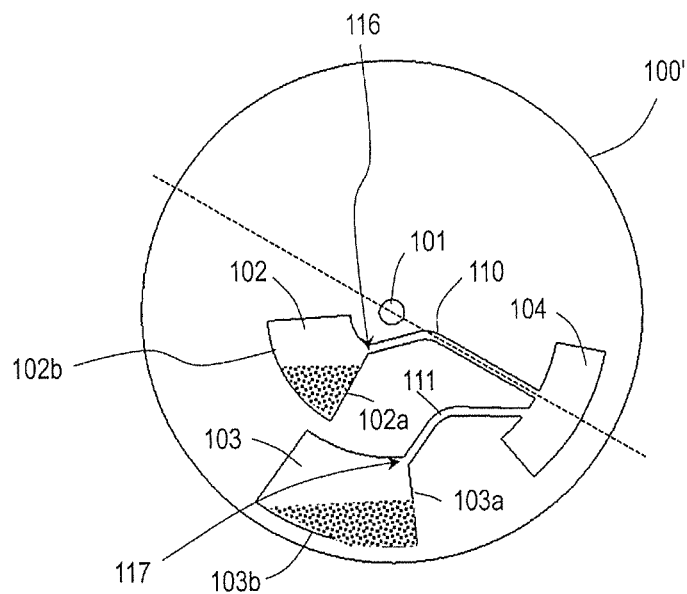
FIG. 14A A diagram showing an exemplary positioning of a first chamber, a second chamber, a first channel, and a second channel of a substrate for sample analysis.
Figure 14B:
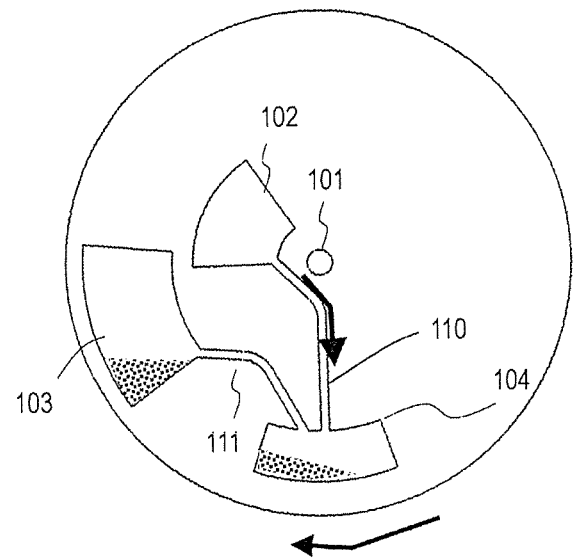
FIG. 14B A diagram showing an example where a first wash solution is transferred in the substrate for sample analysis shown in FIG. 14A.

An instance of the first example is described with reference to FIG. 14A to FIG. 14C. In the example of FIG. 14A, the first boundary position 116 and the second boundary position 117 are in the left one of the two regions of the substrate 100' divided by the straight line connecting the center of the third chamber 104 and the rotation axis 101 (indicated by a broken line). From a state of being retained at an arbitrary predetermined reference angle at which the first wash solution and the second wash solution retained in the first chamber 102 and the second chamber 103 are not transferred to the third chamber via the first channel 110 and the second channel 111, respectively (FIG. 14A), the substrate 100' is rotated clockwise, and as the rotation angle is changed to the first angle, the first wash solution can be transferred from the first chamber 102 to the third chamber 104 (FIG. 14B).

Figure 14C:
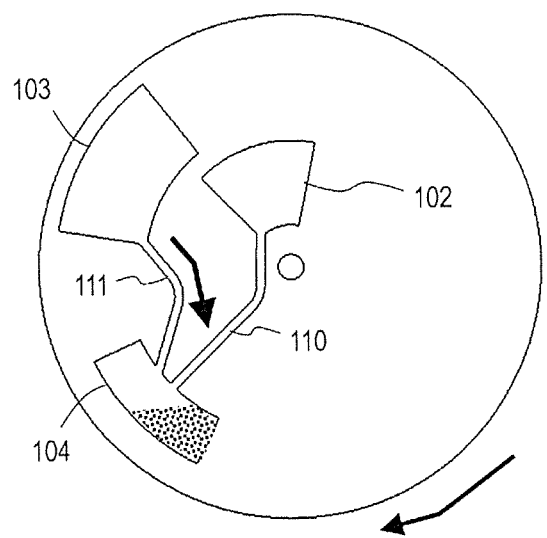
FIG. 14C A diagram showing an example where a second wash solution is transferred in the substrate for sample analysis shown in FIG. 14A.

Moreover, from the state in which the substrate 100' is retained at an arbitrary predetermined reference angle at which the first wash solution and the second wash solution retained in the first chamber 102 and the second chamber 103 are not transferred to the third chamber via the first channel 110 and the second channel 111, respectively (FIG. 14A), the substrate 100' is rotated clockwise, and as the rotation angle is changed to a second angle having a greater absolute value than does the first angle, the second wash solution can be transferred from the second chamber 103 to the third chamber 104 (FIG. 14C).

Thus, in the first example, by rotating the substrate 100' in an identical direction (i.e., clockwise in the example of FIG. 14A), the first wash solution in the first chamber 102 and the second wash solution in the second chamber 103 can be transferred to the third chamber 104 at different points in time.

In a second example, in the first chamber 102, the first boundary position 116 is more distant from the rotation axis 101 than is the first side face 102a; and in the second chamber 103, the second boundary position 117 is more distant from the rotation axis 101 than is the second side face 103a. The substrate 100' is supported so that the rotation axis 101 is inclined at an angle which is greater than 0° but not more than 90° with respect to the direction of gravity, and retained at an arbitrary predetermined reference angle at which the first wash solution and the second wash solution retained in the first chamber 102 and the second chamber 103 are not transferred to the third chamber via the first channel 110 and the second channel 111, respectively. When the substrate 100' in this state is viewed from a direction which is parallel to the rotation axis 101, the first boundary position 116 and the second boundary position 117 are on either the right or left side on the substrate 100', i.e., in one of the two regions divided by a straight line connecting the center of the third chamber 104 and the rotation axis 101.

Figure 15A:
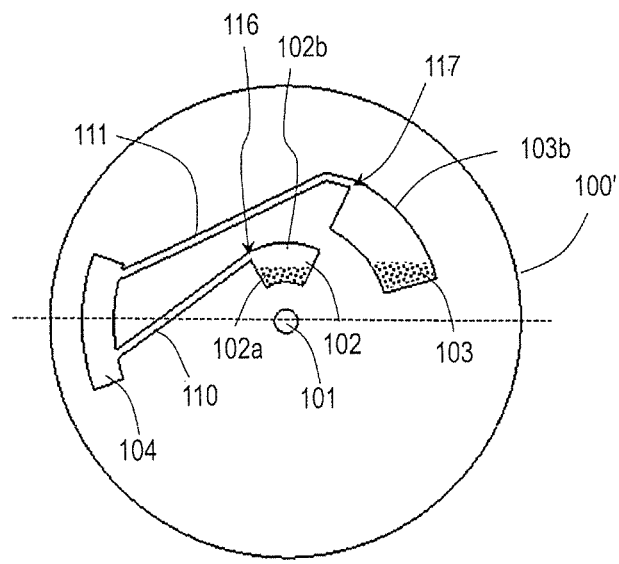
FIG. 15A A diagram showing an exemplary positioning of a first chamber, a second chamber, a first channel, and a second channel of a substrate for sample analysis.
Figure 15B:
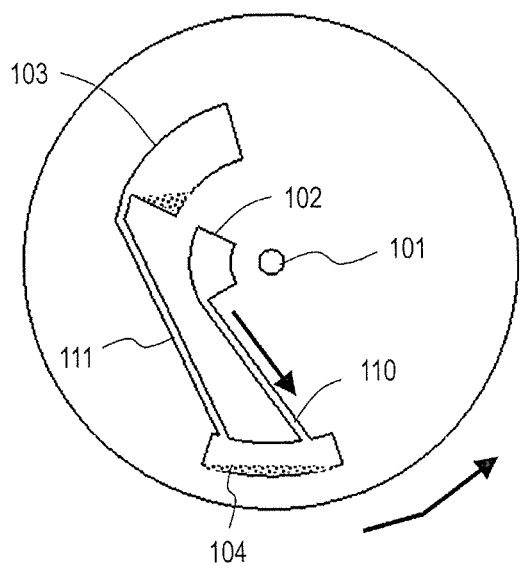
FIG. 15B A diagram showing an example where a first wash solution is transferred in the substrate for sample analysis shown in FIG. 14A.

An instance of the second example is described with reference to FIG. 15A to FIG. 15C. In the example of FIG. 15A, the first boundary position 116 and the second boundary position 117 are in the left one of the two regions of the substrate 100' divided by the straight line connecting the center of the third chamber 104 and the rotation axis 101 (indicated by a broken line). From a state of being retained at an arbitrary predetermined reference angle at which the first wash solution and the second wash solution retained in the first chamber 102 and the second chamber 103 are not transferred to the third chamber via the first channel 110 and the second channel 111, respectively (FIG. 15A), the substrate 100' is rotated counterclockwise, and as the rotation angle is changed to the first angle, the first wash solution can be transferred from the first chamber 102 to the third chamber 104 (FIG. 15B).

Figure 15C:
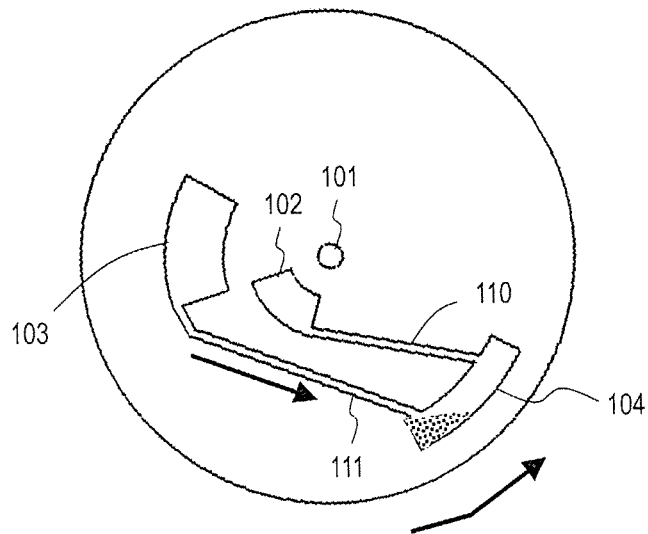
FIG. 15C A diagram showing an example where a second wash solution is transferred in the substrate for sample analysis shown in FIG. 14A.

Moreover, from the state in which the substrate 100' is retained at an arbitrary predetermined reference angle at which the first wash solution and the second wash solution retained in the first chamber 102 and the second chamber 103 are not transferred to the third chamber via the first channel 110 and the second channel 111, respectively (FIG. 15A), the substrate 100' is rotated counterclockwise, and as the rotation angle is changed to a second angle having a greater absolute value than does the first angle, the second wash solution can be transferred from the second chamber 103 to the third chamber 104 (FIG. 15C).

Thus, in the second example, by rotating the substrate 100' in an identical direction (i.e., counterclockwise in the example of FIG. 15A), the first wash solution in the first chamber 102 and the second wash solution in the second chamber 103 can be transferred to the third chamber 104 at different points in time.

In a third example, in the first chamber 102, the first boundary position 116 is closer to the rotation axis 101 than is the first side face 102a; and in the second chamber 103, the second boundary position 117 is closer to the rotation axis 101 than is the second side face 103a. The substrate 100' is supported so that the rotation axis 101 is inclined at an angle which is greater than 0° but not more than 90° with respect to the direction of gravity, and retained at an arbitrary predetermined reference angle at which the first wash solution and the second wash solution retained in the first chamber 102 and the second chamber 103 are not transferred to the third chamber via the first channel 110 and the second channel 111, respectively. When the substrate 100' in this state is viewed from a direction which is parallel to the rotation axis 101, the first boundary position 116 and the second boundary position 117 are on different (right or left) sides on the substrate 100', i.e., so as to be respectively in the two regions divided by the straight line connecting the center of the third chamber 104 and the rotation axis 101.

Figure 16A:
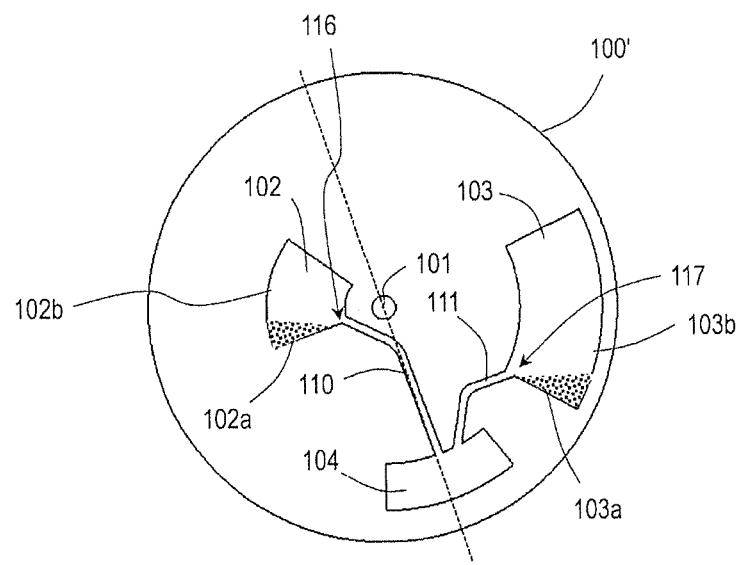
FIG. 16A A diagram showing an exemplary positioning of a first chamber, a second chamber, a first channel, and a second channel of a substrate for sample analysis.
Figure 16B:
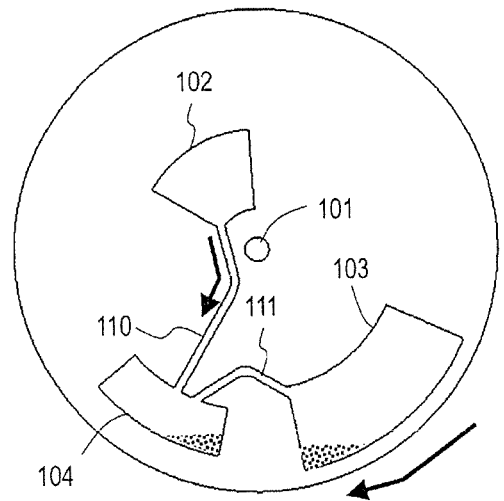
FIG. 16B A diagram showing an example where a first wash solution is transferred in the substrate for sample analysis shown in FIG. 14A.

An instance of the third example is described with reference to FIG. 16A to FIG. 16C. In the example of FIG. 16A, the first boundary position 116 is in the left one of the two regions of the substrate 100' divided by the straight line connecting the center of the third chamber 104 and the rotation axis 101 (indicated by a broken line), while the second boundary position 117 is in the right one. From a state of being retained at an arbitrary predetermined reference angle at which the first wash solution and the second wash solution retained in the first chamber 102 and the second chamber 103 are not transferred to the third chamber via the first channel 110 and the second channel 111, respectively (FIG. 16A), the substrate 100' is rotated clockwise, and as the rotation angle is changed to the first angle, the first wash solution can be transferred from the first chamber 102 to the third chamber 104 (FIG. 16B).

Figure 16C:
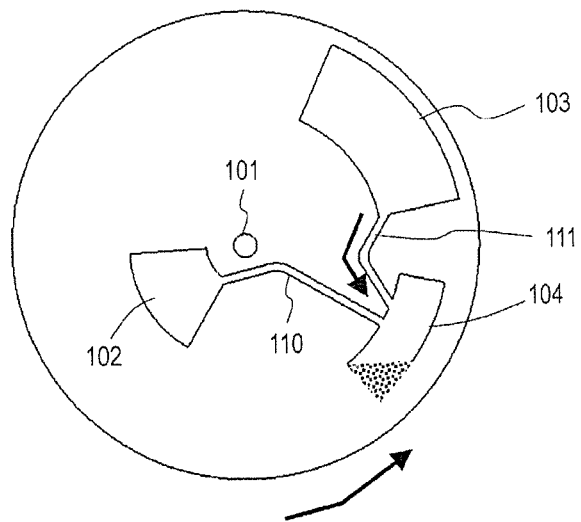
FIG. 16C A diagram showing an example where a second wash solution is transferred in the substrate for sample analysis shown in FIG. 14A.

Moreover, from the state in which the substrate 100' is retained at an arbitrary predetermined reference angle at which the first wash solution and the second wash solution retained in the first chamber 102 and the second chamber 103 are not transferred to the third chamber via the first channel 110 and the second channel 111, respectively (FIG. 16A), the substrate 100' is rotated counterclockwise, and as the rotation angle is changed to the second angle, the second wash solution can be transferred from the second chamber 103 to the third chamber 104 (FIG. 16C).

Thus, in the third example, by rotating the substrate 100' in opposite directions (in the example of FIG. 16A, clockwise for the first chamber 102 and counterclockwise for the second chamber 103), the first wash solution and the second wash solution in the first chamber 102 and the second chamber 103 can be transferred to the third chamber 104 at different points in time.

In a fourth example, in the first chamber 102, the first boundary position 116 is more distant from the rotation axis 101 than is the first side face 102a; and in the second chamber 103, the second boundary position 117 is more distant from the rotation axis 101 than is the second side face 103a. The substrate 100' is supported so that the rotation axis 101 is inclined at an angle which is greater than 0° but not more than 90° with respect to the direction of gravity, and retained at an arbitrary predetermined reference angle at which the first wash solution and the second wash solution retained in the first chamber 102 and the second chamber 103 are not transferred to the third chamber via the first channel 110 and the second channel 111, respectively. When the substrate 100' in this state is viewed from a direction which is parallel to the rotation axis 101, the first boundary position 116 and the second boundary position 117 are on different (right or left) sides on the substrate 100', i.e., so as to be respectively in the two regions divided by the straight line connecting the center of the third chamber 104 and the rotation axis 101.

In the fourth example, the method of moving the first wash solution and the second wash solution is similar to that of the third example. In other words, similarly to the third example, by rotating the substrate 100' in opposite directions, the first wash solution and the second wash solution in the first chamber 102 and the second chamber 103 can be transferred to the third chamber 104 at different points in time.

In a fifth example, in the first chamber 102, the first boundary position 116 is closer to the rotation axis 101 than is the first side face 102a; and in the second chamber 103, the second boundary position 117 is more distant from the rotation axis 101 than is the second side face 103a. The substrate 100' is supported so that the rotation axis 101 is inclined at an angle which is greater than 0° but not more than 90° with respect to the direction of gravity, and retained at an arbitrary predetermined reference angle at which the first wash solution and the second wash solution retained in the first chamber 102 and the second chamber 103 are not transferred to the third chamber via the first channel 110 and the second channel 111, respectively. When the substrate 100' in this state is viewed from a direction which is parallel to the rotation axis 101, the first boundary position 116 and the second boundary position 117 are on different (right or left) sides on the substrate 100', i.e., so as to be respectively in the two regions divided by the straight line connecting the center of the third chamber 104 and the rotation axis 101.

Figure 17A:
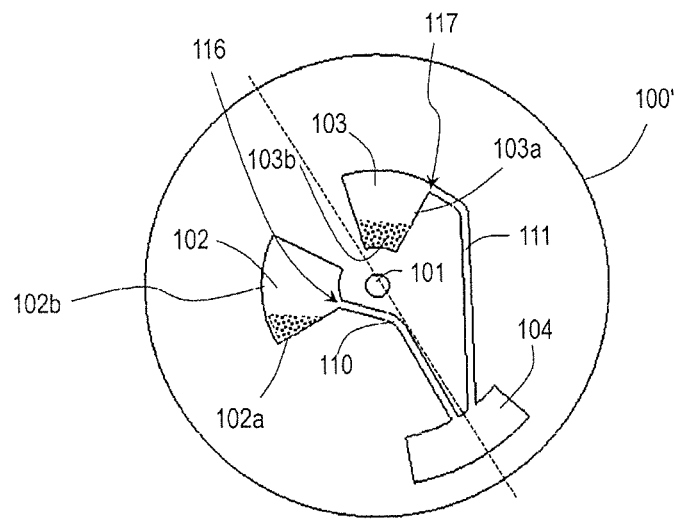
FIG. 17A A diagram showing an exemplary positioning of a first chamber, a second chamber, a first channel, and a second channel of a substrate for sample analysis.
Figure 17B:
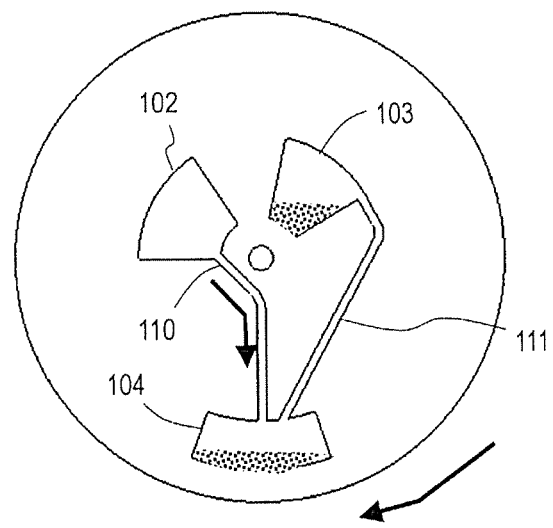
FIG. 17B A diagram showing an example where a first wash solution is transferred in the substrate for sample analysis shown in FIG. 14A.

An instance of the fifth example is described with reference to FIG. 17A to FIG. 17C. In the example of FIG. 17A, the first boundary position 116 is in the left one of the two regions of the substrate 100' divided by the straight line connecting the center of the third chamber 104 and the rotation axis 101 (indicated by a broken line), while the second boundary position 117 is in the right one. From a state of being retained at an arbitrary predetermined reference angle at which the first wash solution and the second wash solution retained in the first chamber 102 and the second chamber 103 are not transferred to the third chamber via the first channel 110 and the second channel 111, respectively (FIG. 17A), the substrate 100' is rotated clockwise, and as the rotation angle is changed to the first angle, the first wash solution can be transferred from the first chamber 102 to the third chamber 104 (FIG. 17B).

Figure 17C:
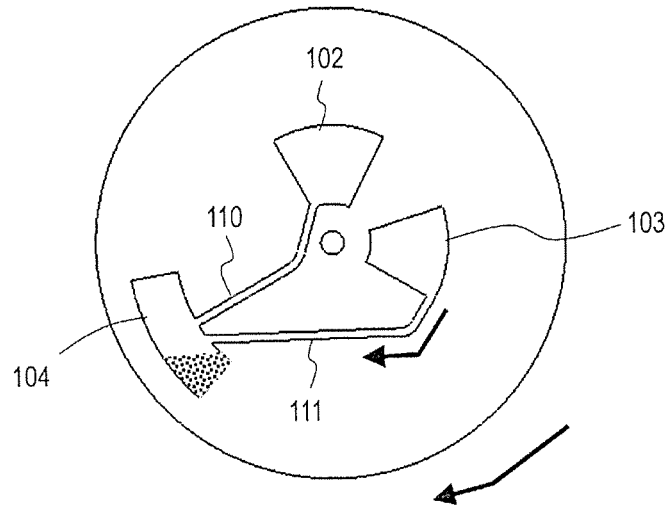
FIG. 17C A diagram showing an example where a second wash solution is transferred in the substrate for sample analysis shown in FIG. 14A.

Moreover, from the state in which the substrate 100' is retained at an arbitrary predetermined reference angle at which the first wash solution and the second wash solution retained in the first chamber 102 and the second chamber 103 are not transferred to the third chamber via the first channel 110 and the second channel 111, respectively (FIG. 17A), the substrate 100' is rotated clockwise, and as the rotation angle is changed to a second angle having a greater absolute value than does the first angle, the second wash solution can be transferred from the second chamber 103 to the third chamber 104 (FIG. 17C).

Thus, in the fifth example, by rotating the substrate 100' in an identical direction (i.e., clockwise in the example of FIG. 17A), the first wash solution in the first chamber 102 and the second wash solution in the second chamber 103 can be transferred to the third chamber 104 at different points in time.

In a sixth example, in the first chamber 102, the first boundary position 116 is more distant from the rotation axis 101 than is the first side face 102a; and in the second chamber 103, the second boundary position 117 is closer to the rotation axis 101 than is the second side face 103a. The substrate 100' is supported so that the rotation axis 101 is inclined at an angle which is greater than 0° but not more than 90° with respect to the direction of gravity, and retained at an arbitrary predetermined reference angle at which the first wash solution and the second wash solution retained in the first chamber 102 and the second chamber 103 are not transferred to the third chamber via the first channel 110 and the second channel 111, respectively. When the substrate 100' in this state is viewed from a direction which is parallel to the rotation axis 101, the first boundary position 116 and the second boundary position 117 are on different (right or left) sides on the substrate 100', i.e., so as to be respectively in the two regions divided by the straight line connecting the center of the third chamber 104 and the rotation axis 101.

In the sixth example, the method of moving the first wash solution and the second wash solution is similar to that of the fifth example.

Thus, similarly to the fifth example, by rotating the substrate 100' in the same direction, the first wash solution and the second wash solution in the first chamber 102 and the second chamber 103 can be transferred to the third chamber 104 at different points in time.

In a seventh example, in the first chamber 102, the first boundary position 116 is closer to the rotation axis 101 than is the first side face 102a; and in the second chamber 103, the second boundary position 117 is more distant from the rotation axis than is the second side face 103a. The substrate 100' is supported so that the rotation axis 101 is inclined at an angle which is greater than 0° but not more than 90° with respect to the direction of gravity, and retained at an arbitrary predetermined reference angle at which the first wash solution and the second wash solution retained in the first chamber 102 and the second chamber 103 are not transferred to the third chamber via the first channel 110 and the second channel 111, respectively. When the substrate 100' in this state is viewed from a direction which is parallel to the rotation axis 101, the first boundary position 116 and the second boundary position 117 are on either the right or left side on the substrate 100', i.e., in one of the two regions divided by a straight line connecting the center of the third chamber 104 and the rotation axis 101.

Figure 18A:
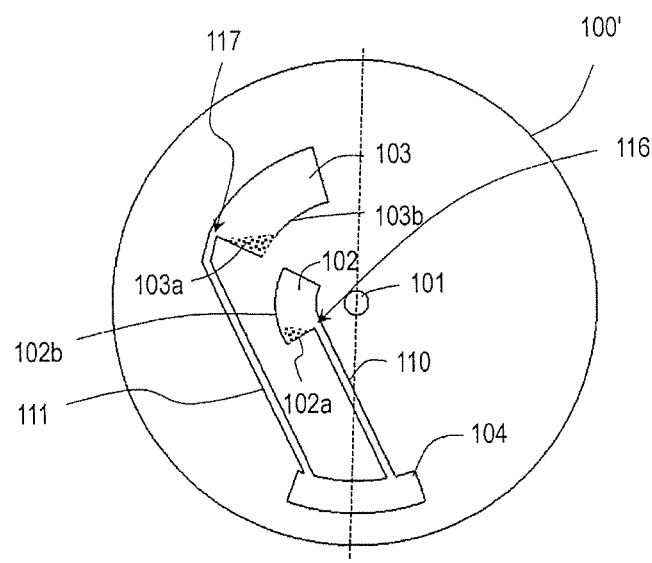
FIG. 18A A diagram showing an exemplary positioning of a first chamber, a second chamber, a first channel, and a second channel of a substrate for sample analysis.
Figure 18B:
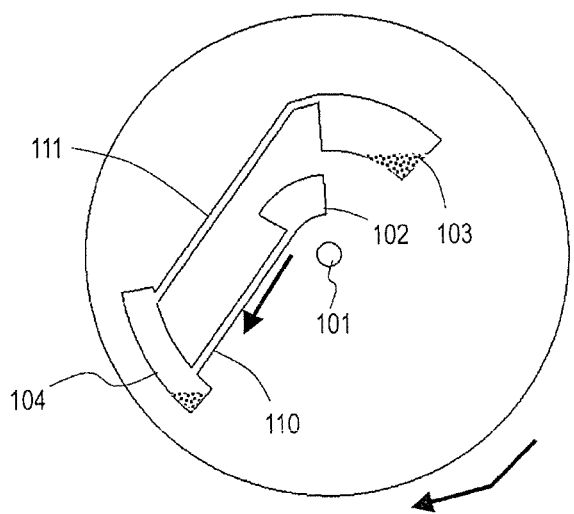
FIG. 18B A diagram showing an example where a first wash solution is transferred in the substrate for sample analysis shown in FIG. 14A.

An instance of the seventh example is described with reference to FIG. 18A to FIG. 18C. In the example of FIG. 18A, the first boundary position 116 and the second boundary position 117 are in the left one of the two regions of the substrate 100' divided by the straight line connecting the center of the third chamber 104 and the rotation axis 101 (indicated by a broken line). From a state of being retained at an arbitrary predetermined reference angle at which the first wash solution and the second wash solution retained in the first chamber 102 and the second chamber 103 are not transferred to the third chamber via the first channel 110 and the second channel 111, respectively (FIG. 18A), the substrate 100' is rotated clockwise, and as the rotation angle is changed to the first angle, the first wash solution can be transferred from the first chamber 102 to the third chamber 104 (FIG. 18B).

Figure 18C:
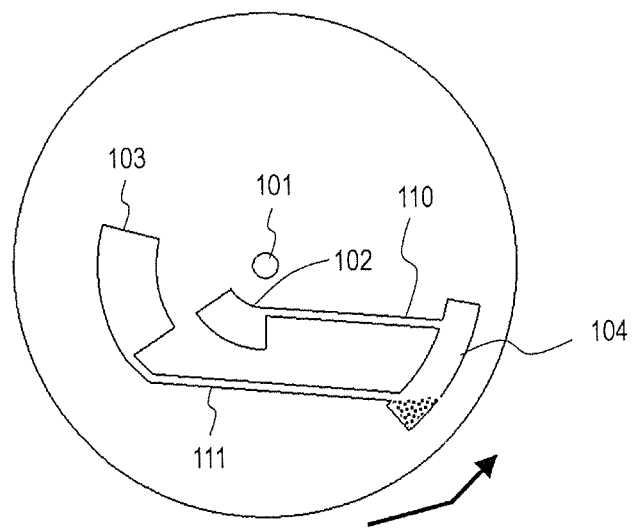
FIG. 18C A diagram showing an example where a second wash solution is transferred in the substrate for sample analysis shown in FIG. 14A.

Moreover, from the state in which the substrate 100' is retained at an arbitrary predetermined reference angle at which the first wash solution and the second wash solution retained in the first chamber 102 and the second chamber 103 are not transferred to the third chamber via the first channel 110 and the second channel 111, respectively (FIG. 18A), the substrate 100' is rotated counterclockwise, and as the rotation angle is changed to the second angle, the second wash solution can be transferred from the second chamber 103 to the third chamber 104 (FIG. 18C).

Thus, in the seventh example, by rotating the substrate 100' in an identical direction (i.e., counterclockwise in the example of FIG. 18A), the first wash solution in the first chamber 102 and the second wash solution in the second chamber 103 can be transferred to the third chamber 104 at different points in time.

In an eighth example, in the first chamber 102, the first boundary position 116 is more distant from the rotation axis 101 than is the first side face 102a; and in the second chamber 103, the second boundary position 117 is closer to the rotation axis than is the second side face 103a. The substrate 100' is supported so that the rotation axis 101 is inclined at an angle which is greater than 0° but not more than 90° with respect to the direction of gravity, and retained at an arbitrary predetermined reference angle at which the first wash solution and the second wash solution retained in the first chamber 102 and the second chamber 103 are not transferred to the third chamber via the first channel 110 and the second channel 111, respectively. When the substrate 100' in this state is viewed from a direction which is parallel to the rotation axis 101, the first boundary position 116 and the second boundary position 117 are on either the right or left side on the substrate 100', i.e., in one of the two regions divided by a straight line connecting the center of the third chamber 104 and the rotation axis 101.

In the eighth example, the method of moving the first wash solution and the second wash solution is similar to that of the seventh example. In other words, similarly to the seventh example, the first wash solution and the second wash solution in the first chamber 102 and the second chamber 103 can be transferred to the third chamber 104 at different points in time by rotating the substrate 100' in opposite directions.

The first to eighth examples of transfer of liquids are exemplary; the timing of transfer of the first wash solution and the second wash solution to the third chamber 104 can be controlled based on the shapes of the first side face 102a of the first chamber 102 and the second side face 103a of the second chamber 103.

Moreover, the timing of transfer of the first wash solution and the second wash solution to the third chamber 104 can be controlled based on the amount of first wash solution to be retained in the first chamber 102 and the second chamber 103 (i.e., the amount of first wash solution in the first storage chamber 108) and the amount of second wash solution (i.e., the amount of second wash solution in the second storage chamber 109). For example, given two substrates 100 for sample analysis which are identical in structure except for the shapes of the first side face 102a of the first chamber 102 and the second side face 103a of the second chamber 103, the first wash solution may be transferred to the third chamber 104 first or the second wash solution may be transferred to the third chamber 104 first, based on the different shapes of the first side face 102a and the second side face 103a. Moreover, for example, even if the substrate 100 for sample analysis has the same structure and the same rotation control is applied to the substrate 100 for sample analysis, the first wash solution may be transferred to the third chamber 104 first or the second wash solution may be transferred to the third chamber 104 first, depending on the amount of first wash solution and the amount of second wash solution to be retained in the first chamber 102 and the second chamber 103.

While a wash solution is retained in at least one of the first chamber 102 and the second chamber 103, if any other liquid is to be transferred through rotation of the substrate 100 for sample analysis (due to centrifugal force), there is a possibility that the wash solution may be transferred to the third chamber 104 with unintended timing. In order to restrain the wash solution from being transferred to the third chamber 104 with such unintended timing, it is preferable that the first boundary position 116 in the first chamber 102 is closer to the rotation axis 101 than is the first side face 102a. Moreover, it is preferable that the second boundary position 117 in the second chamber 103 is closer to the rotation axis 101 than is the second side face 103a. The reason is that, as the substrate 100 for sample analysis is rotated in order to transfer other liquids due to centrifugal force, centrifugal force will act also on the first wash solution in the first chamber 102 and the second wash solution in the second chamber 103 so that they will be retained by the third side face 102b and the fourth side face 13b, which are located more distant from the rotation axis 101 than are the first boundary position 116 and the second boundary position 117 respectively, thus causing the liquid surfaces of the first wash solution and the second wash solution to be farther away from the openings of the first channel 110 and the second channel 111.

Moreover, the direction of rotation of the substrate 100 for sample analysis may also affect a wash solution's transfer to the third chamber 104 with unintended timing. For example, in the case where the substrate 100 for sample analysis is of the implementation as shown in FIG. 14A for the first example, if the substrate 100 for sample analysis is rotated in counterclockwise direction from the state shown in FIG. 14A, changing the rotation angle of the substrate 100 for sample analysis to the first angle as shown in FIG. 14B may possibly cause the first wash solution and the second wash solution to be transferred to the third chamber 104 during rotation. Therefore, in the case where the rotation angle of the substrate 100' is to be changed to the first angle and the second angle, it is preferable to take the rotation direction also into account.

INDUSTRIAL APPLICABILITY

The substrate for sample analysis, sample analysis device, sample analysis system, and program for a sample analysis system disclosed herein are applicable to the analysis of a specific component within an analyte by utilizing various reactions.

REFERENCE SIGNS LIST 100 substrate for sample analysis
100' substrate
100a base substrate
100b cover substrate
101 rotation axis
102 first chamber
102a first side face
102b third side face
103 second chamber
103a second side face
103b fourth side face
104 third chamber
105 fourth chamber
106 magnet
107 reaction chamber
108 first storage chamber
109 second storage chamber
110 first channel
111 second channel
112 third channel
113 fourth channel
114 fifth channel
115 sixth channel
116 first boundary position
117 second boundary position
118 air hole
119 opening
121 third storage chamber
122 seventh channel
123 fifth chamber
124 eighth channel
200 sample analysis device
201 motor
201a turntable
203 origin detector
204 rotation angle detection circuit
205 control circuit
206 drive circuit
207 optical measurement unit
302 magnetic particles
304 primary antibody
305 magnetic-particle-immobilized antibody
306 antigen
307 label substance
308 labeled antibody
310 composite
501 sample analysis system

The invention claimed is:

1. A substrate for sample analysis on which transfer of liquids is to occur with rotational motion, the substrate for sample analysis comprising:
a substrate having a rotation axis;
a first chamber and a second chamber being located in the substrate and respectively having a first space and a second space for retaining a first liquid and a second liquid;
a third chamber being located in the substrate and having a third space for retaining the liquids to be discharged from the first chamber and the second chamber;
a first channel having a path connecting the first chamber and the third chamber in the substrate to transfer the first liquid; and
a second channel having a path connecting the second chamber and the third chamber in the substrate to transfer the second liquid, wherein,
in rotating the substrate clockwise or counterclockwise around the rotation axis while supporting the substrate so that the rotation axis of the substrate is inclined at an angle which is greater than 0° but not more than 90° with respect to a direction of gravity,
when the substrate is rotated by an angle A1 from an arbitrary predetermined reference angle at which the first liquid and the second liquid retained in the first chamber and the second chamber are not transferred to the third chamber via the first channel and the second channel, respectively,
a first predetermined amount of first liquid moves from the first chamber to the third chamber, and a second predetermined amount of second liquid moves from the second chamber to the third chamber; and when the substrate is further rotated by an angle A2 from the angle A1,
a third predetermined amount of first liquid moves from the first chamber to the third chamber, and
a fourth predetermined amount of second liquid moves from the second chamber to the third chamber.

2. The substrate for sample analysis of claim 1, wherein the first predetermined amount is the entire amount of first liquid that is retained in the first chamber, and the third predetermined amount is zero.

3. The substrate for sample analysis of claim 1, wherein,
the first predetermined amount is the entire amount of first liquid that is retained in the first chamber;
the second predetermined amount is zero;
the third predetermined amount is zero; and
the fourth predetermined amount is the entire amount of second liquid that is retained in the second chamber.

4. The substrate for sample analysis of claim 1, further comprising a magnet located near the third chamber.

5. The substrate for sample analysis of claim 1, wherein the first channel and the second channel respectively transfer the first liquid and the second liquid based on gravity.

6. The substrate for sample analysis of claim 5, wherein, when the substrate is retained at the arbitrary predetermined reference angle while supporting the substrate so that the rotation axis of the substrate is inclined at an angle which is greater than 0° but not more than 90° with respect to the direction of gravity,
the third chamber is situated below the first chamber and the second chamber along the direction of gravity.

7. The substrate for sample analysis of claim 1, wherein the second predetermined amount is zero.

8. The substrate for sample analysis of claim 7, wherein the fourth predetermined amount is the entire amount of second liquid that is retained in the second chamber.

9. A sample analysis system comprising:
the substrate for sample analysis of claim 1; and
a sample analysis device, including
a motor to rotate the substrate for sample analysis around the rotation axis in a state where the rotation axis is inclined at an angle which is greater than 0° but not more than 90° with respect to the direction of gravity,
an angle detection circuit to detect an angle of a shaft of the motor,
a drive circuit to control rotation and a stopping angle of the motor based on a result of detection by the angle detection circuit, and
a control circuit including an arithmetic unit, a memory, and a program which is stored in the memory and executable by the arithmetic unit, to control based on the program an operation of the motor, the angle detection circuit, the origin detector, and the drive circuit,
wherein,
when the substrate for sample analysis with the first chamber and the second chamber being filled respectively with the first liquid and the second liquid is placed on a turntable of the sample analysis device,
the program
(a) stops the substrate for sample analysis at a predetermined first angle to transfer the first liquid in the first chamber through the first channel to the third chamber, and
(b) stops the substrate for sample analysis at a predetermined second angle to transfer the second liquid in the second chamber through the second channel to the third chamber.

10. The sample analysis system of claim 9, wherein,
the substrate for sample analysis further includes
a fourth chamber being in the substrate located more distant from the rotation axis than is the third chamber and having a fourth space for retaining at least one of the first liquid or the second liquid to be discharged from the third chamber, and
a third channel being located in the substrate and having a path connecting the third chamber and the fourth chamber, the third channel capable of being filled via capillary action with the liquid that is retained in the third space; and
between the processes (a) and (b), the program,
(c) with a centrifugal force due to rotation of the substrate, rotates the substrate for sample analysis at a rate causing a centrifugal force which is stronger than a capillary force to act on the liquid filling the third channel, to move the first liquid in the third chamber through the third channel to the fourth chamber.

11. The sample analysis system of claim 9, wherein, after the process (b), the program,
(d) with a centrifugal force due to rotation of the substrate, rotates the substrate for sample analysis at a rate causing a centrifugal force which is stronger than a capillary force to act on the liquid filling the third channel, to move the second liquid in the third chamber through the third channel to the fourth chamber.

12. A sample analysis device comprising:
a motor to rotate the substrate for sample analysis of claim 1 around the rotation axis in a state where the rotation axis is inclined at an angle which is greater than 0° but not more than 90° with respect to the direction of gravity;
an angle detection circuit to detect an angle of a shaft of the motor;
a drive circuit to control rotation and a stopping angle of the motor based on a result of detection by the angle detection circuit; and
a control circuit including an arithmetic unit, a memory, and a program which is stored in the memory and executable by the arithmetic unit, to control based on the program an operation of the motor, the angle detection circuit, and the drive circuit,
wherein,
when the substrate for sample analysis with the first chamber and the second chamber being filled respectively with the first liquid and the second liquid is placed on a turntable of the sample analysis device,
the program
(a) stops the substrate for sample analysis at a predetermined first angle to transfer the first liquid in the first chamber through the first channel to the third chamber, and
(b) stops the substrate for sample analysis at a predetermined second angle to transfer the second liquid in the second chamber through the second channel to the third chamber.

13. The sample analysis device of claim 12, wherein,
the substrate for sample analysis further includes
a fourth chamber being in the substrate located more distant from the rotation axis than is the third chamber and having a fourth space for retaining at least one of the first liquid or the second liquid to be discharged from the third chamber, and
a third channel being located in the substrate and having a path connecting the third chamber and the fourth chamber, the third channel capable of being filled via capillary action with the liquid that is retained in the third space; and between the processes (a) and (b), the program, (c) with a centrifugal force due to rotation of the substrate, rotates the substrate for sample analysis at a rate causing a centrifugal force which is stronger than a capillary force to act on the liquid filling the third channel, to move the first liquid in the third chamber through the third channel to the fourth chamber.

14. The sample analysis device of claim 12, wherein, after the process (b), the program, (d) with a centrifugal force due to rotation of the substrate, rotates the substrate for sample analysis at a rate causing a centrifugal force which is stronger than a capillary force to act on the liquid filling the third channel, to move the second liquid in the third chamber through the third channel to the fourth chamber.

15. A non-transitory computer-readable storage medium storing a program for a sample analysis system comprising:
the substrate for sample analysis of claim 1; and
a sample analysis device, including
a motor to rotate the substrate for sample analysis around the rotation axis in a state where the rotation axis is inclined at an angle which is greater than 0° but not more than 90° with respect to the direction of gravity,
an angle detection circuit to detect an angle of a shaft of the motor,
a drive circuit to control rotation and a stopping angle of the motor based on a result of detection by the angle detection circuit, and
a control circuit including an arithmetic unit, a memory, and a program which is stored in the memory and executable by the arithmetic unit, to control based on the program an operation of the motor, the angle detection circuit, the origin detector, and the drive circuit,
wherein,
when the substrate for sample analysis with the first chamber and the second chamber being filled respectively with the first liquid and the second liquid is placed on a turntable of the sample analysis device, the program
(a) stops the substrate for sample analysis at a predetermined first angle to transfer the first liquid in the first chamber through the first channel to the third chamber, and
(b) stops the substrate for sample analysis at a predetermined second angle to transfer the second liquid in the second chamber through the second channel to the third chamber.

16. The non-transitory computer-readable storage medium of claim 15, wherein,
the substrate for sample analysis further includes
a fourth chamber being in the substrate located more distant from the rotation axis than is the third chamber and having a fourth space for retaining at least one of the first liquid or the second liquid to be discharged from the third chamber, and
a third channel being located in the substrate and having a path connecting the third chamber and the fourth chamber, the third channel capable of being filled via capillary action with the liquid that is retained in the third space; and
between the processes (a) and (b), the program, (c) with a centrifugal force due to rotation of the substrate, rotates the substrate for sample analysis at a rate causing a centrifugal force which is stronger than a capillary force to act on the liquid filling the third channel, to move the first liquid in the third chamber through the third channel to the fourth chamber.

17. The non-transitory computer-readable storage medium of claim 15, wherein, after the process (b), the program, (d) with a centrifugal force due to rotation of the substrate, rotates the substrate for sample analysis at a rate causing a centrifugal force which is stronger than a capillary force to act on the liquid filling the third channel, to move the second liquid in the third chamber through the third channel to the fourth chamber.

18. The substrate for sample analysis of claim 1, wherein, the substrate includes
a first side face defining a portion of the first space in the substrate and adjoining the first channel, and a third side face adjoining the first side face, and
a second side face defining a portion of the second space in the substrate and adjoining the second channel, and a fourth side face adjoining the second side face; and
when the substrate is retained at the arbitrary predetermined reference angle while supporting the substrate so that the rotation axis of the substrate is inclined at an angle which is greater than 0° but not more than 90° with respect to the direction of gravity,
the first chamber retains the first liquid at least with the first side face and the third side face, and
the second chamber retains the second liquid at least with the second side face and the fourth side face.

19. The substrate for sample analysis of claim 18, wherein a first boundary position between the first side face and the first channel is defined by a boundary between a liquid surface of a first wash solution and the first channel or the first side face that exists when, in rotating the substrate from the arbitrary predetermined reference angle to the angle A1, the first liquid first begins to move toward the third chamber at a position along a predetermined thickness direction.

20. The substrate for sample analysis of claim 19, wherein a second boundary position between the second side face and the second channel is defined by a boundary between a liquid surface of a second wash solution and the second channel or the second side face that exists when, in rotating the substrate from the arbitrary predetermined reference angle to the angle A2, the second liquid first begins to move toward the third chamber at a position along the predetermined thickness direction.

21. The substrate for sample analysis of claim 20, wherein,
in a case where the first boundary position is closer to the rotation axis than is the first side face and the second boundary position is closer to the rotation axis than is the second side face, or
in a case where the first boundary position is more distant from the rotation axis than is the first side face and the second boundary position is more distant from the rotation axis than is the second side face,
when the substrate is viewed from a direction which is parallel to the rotation axis in a state where the substrate is retained at the arbitrary predetermined reference angle while supporting the substrate so that the rotation axis of the substrate is inclined at an angle which is greater than 0° but not more than 90° with respect to the direction of gravity, the first boundary position and second boundary position are on either a right or left side on the substrate; and a direction of rotation in which the substrate is rotated by the angle A1 from the arbitrary predetermined reference angle and a direction of rotation in which the substrate is rotated by the angle A2 from the angle A1 are an identical direction.

22. The substrate for sample analysis of claim 20, wherein,
   in a case where the first boundary position is closer to the rotation axis than is the first side face and the second boundary position is closer to the rotation axis than is the second side face, or
   in a case where the first boundary position is more distant from the rotation axis than is the first side face and the second boundary position is more distant from the rotation axis than is the second side face,
   when the substrate is viewed from a direction which is parallel to the rotation axis in a state where the substrate is retained at the arbitrary predetermined reference angle while supporting the substrate so that the rotation axis of the substrate is inclined at an angle which is greater than 0° but not more than 90° with respect to the direction of gravity, the first boundary position and second boundary position are respectively on different right or left sides on the substrate,
   a direction of rotation in which the substrate is rotated by the angle A1 from the arbitrary predetermined reference angle and a direction of rotation in which the substrate is rotated by the angle A2 from the angle A1 are opposite directions.

23. The substrate for sample analysis of claim 20, wherein,
   in a case where the first boundary position is closer to the rotation axis than is the first side face and the second boundary position is more distant from the rotation axis than is the second side face, or
   in a case where the first boundary position is more distant from the rotation axis than is the first side face and the second boundary position is closer to the rotation axis than is the second side face,
   when the substrate is viewed from a direction which is parallel to the rotation axis in a state where the substrate is retained at the arbitrary predetermined reference angle while supporting the substrate so that the rotation axis of the substrate is inclined at an angle which is greater than 0° but not more than 90° with respect to the direction of gravity, the first boundary position and second boundary position respectively on different right or left sides on the substrate; and
   a direction of rotation in which the substrate is rotated by the angle A1 from the arbitrary predetermined reference angle and a direction of rotation in which the substrate is rotated by the angle A2 from the angle A1 are an identical direction.

24. The substrate for sample analysis of claim 20, wherein,
   in a case where the first boundary position is closer to the rotation axis than is the first side face and the second boundary position is more distant from the rotation axis than is the second side face, or
   in a case where the first boundary position is more distant from the rotation axis than is the first side face and the second boundary position is closer to the rotation axis than is the second side face,
   when the substrate is viewed from a direction which is parallel to the rotation axis in a state where the substrate is retained at the arbitrary predetermined reference angle while supporting the substrate so that the rotation axis of the substrate is inclined at an angle which is greater than 0° but not more than 90° with respect to the direction of gravity, the first boundary position and second boundary position are on either a right or left side on the substrate,
   a direction of rotation in which the substrate is rotated by the angle A1 from the arbitrary predetermined reference angle and a direction of rotation in which the substrate is rotated by the angle A2 from the angle A1 are opposite directions.

* * * * *